(12) United States Patent
El Ali et al.

(10) Patent No.: US 11,236,118 B1
(45) Date of Patent: Feb. 1, 2022

(54) SELECTIVE CYCLOCARBONYLATIVE COUPLING OF 2-IODOPHENOLS WITH TERMINAL ALKYNES CATALYZED BY BRIDGED BIS(NHC)PD(II)BR$_2$ CATALYSTS

(71) Applicants: King Fahd University of Petroleum & Minerals, Dhahran (SA); Saudi Arabian Oil Company, Dhahran (SA)

(72) Inventors: Bassam El Ali, Dhahran (SA); Waseem Mansour, Dhahran (SA); Mohammed Fettouhi, Dhahran (SA)

(73) Assignee: King Fahd University of Petroleum & Minerals, Kingdom of Saudi (SA)

( * ) Notice: Subject to any disclaimer, the term of this patent is extended or adjusted under 35 U.S.C. 154(b) by 0 days.

(21) Appl. No.: 17/094,140

(22) Filed: Nov. 10, 2020

(51) Int. Cl.
C07F 15/00 (2006.01)
B01J 31/30 (2006.01)
B01J 37/22 (2006.01)

(52) U.S. Cl.
CPC ............. C07F 15/006 (2013.01); B01J 31/30 (2013.01); B01J 37/22 (2013.01)

(58) Field of Classification Search
None
See application file for complete search history.

(56) References Cited

U.S. PATENT DOCUMENTS

| | | |
|---|---|---|
| 2007/0073055 A1 | 3/2007 | Organ et al. |
| 2009/0326237 A1 | 12/2009 | Strassner et al. |
| 2019/0016741 A1 | 1/2019 | Hollis et al. |
| 2019/0374933 A1 | 12/2019 | Nolan |

OTHER PUBLICATIONS

Aktaş et al., "Mixed phosphine/N-heterocyclic carbene-palladium complexes: synthesis, characterization, crystal structure and application in the Sonogashira reaction in aqueous media." Transition Metal Chemistry 44.3, 2019, 229-236, 8 pages.

Aktaş et al., "Novel morpholine liganded Pd-based N-heterocyclic carbene complexes: Synthesis, characterization, crystal structure, antidiabetic and anticholinergic properties." Polyhedron 159, 2019, 345-354, 32 pages.

Awuah et al., Access to Flavones via a Microwave-Assisted, One-Pot Sonogashira-Carbonylation-Annulation Reaction Org. Lett. vol. 11, 2009, 3210-3213, 4 pages.

Babu et al., "Synthesis and biological evaluation of novel 8-aminomethylated oroxylin A analogues as alpha-glucosidase inhibitors." Bioorganic & medicinal chemistry letters 18.5, 2008, 1659-1662, 4 pages.

Bai et al., "Carbonylative Sonogashira coupling of terminal alkynes with aryl iodides under atmospheric pressure of CO using Pd (II) MOF as the catalyst." Catalysis Science & Technology 4.9, 2014, 3261-3267, 7 pages.

Baruah et al., "Ru (ii)-Catalyzed C—H activation and annulation of salicylaldehydes with monosubstituted and disubstituted alkynes." Chemical Communications 52.88, 2016, 13004-13007, 4 pages.

Boncel et al., "Michael-type addition of azoles of broad-scale acidity to methyl acrylate." Beilstein journal of organic chemistry 7.1, 2011, 173-178, 6 pages.

Brennführer et al., "Palladium-catalyzed carbonylation reactions of aryl halides and related compounds." Angewandte Chemie International Edition 48.23, 2009, 4114-4133, 20 pages.

Brimble et al., "Pyrans and their Benzo Derivatives: Synthesis." Comprehensive Heterocyclic Chemistry III, 2008, 281 pages.

Chinchilla et al., "The Sonogashira reaction: a booming methodology in synthetic organic chemistry." Chemical reviews 107.3, 2007, 874-922.

Cui et al., "Carbonylative Suzuki coupling reactions of aryl iodides with arylboronic acids over Pd/SiC." Chinese Journal of Catalysis 36.3, 2015, 322-327, 6 pages.

Demirayak et al., "New chroman-4-one/thiochroman-4-one derivatives as potential anticancer agents." Saudi Pharmaceutical Journal 25.7,2017, 1063-1072, 31 pages.

Feng et al., "Carbonylative Sonogashira Coupling of Aryl Iodides with Terminal Alkynes Catalyzed by Palladium Nanoparticles." Journal of the Chinese Chemical Society 65.3, 2018, 337-345.

Ferreira et al., "Flavonoid compounds as reversal agents of the P-glycoprotein-mediated multidrug resistance: biology, chemistry and pharmacology." Phytochemistry Reviews 14.2, 2015, 233-272, 40 pages.

Gadge et al., "Recent developments in palladium catalysed carbonylation reactions." RSC Advances 4.20, 2014, 10367-10389, 23 pages.

Gautam et al., "Aminophosphine Palladium Pincer-Catalyzed Carbonylative Sonogashira and Suzuki-Miyaura Cross-Coupling with High Catalytic Turnovers." ACS omega 4.1, 2019, 1560-1574, 15 pages.

Gautam et al., "Palladacycle-Catalyzed Carbonylative Suzuki-Miyaura Coupling with High Turnover Number and Turnover Frequency." The Journal of organic chemistry 80.15, 2015, 7810-7815, 19 pages.

Gazvoda et al., "A mesoionic bis (Py-tz NHC) palladium (ii) complex catalyses "green" Sonogashira reaction through an unprecedented mechanism." Chemical Communications 52.8, 2016, 1571-1574, 4 pages.

Genelot et al., "Carbonylative Sonogashira coupling in the synthesis of ynones: a study of "boomerang" phenomena." Advanced Synthesis & Catalysis 355.13, 2013, 2604-2616, 14 pages.

Hahn et al., "The Pd (II) complex of a bidentate di (benzimidazol-2-ylidene) ligand." Zeitschrift fur Naturforschung B 59.5, 2004, 541-543, 3 pages.

(Continued)

*Primary Examiner* — Yun Qian
(74) *Attorney, Agent, or Firm* — Fish & Richardson P.C.

(57) ABSTRACT

Palladium catalysts, methods of synthesizing palladium-carbene catalysts, and methods of producing chromones and aurones using palladium-N-heterocyclic carbene (NHC) catalysts are provided. In some implementations, the palladium catalysts include a bridged palladium catalyst with distorted square planar geometry around the center palladium atom. The catalysts can be used in cyclocarbonylative Sonogashira cross-coupling reactions to produce chromones and aurones at a high yield. The selectivity of the catalysts can be adjusted by adjusting reaction conditions.

4 Claims, 14 Drawing Sheets

(56) References Cited

OTHER PUBLICATIONS

Hao et al., "The first heterogeneous carbonylative Sonogashira coupling reaction catalyzed by MCM-41-supported bidentate phosphine palladium (0) complex." Journal of Molecular Catalysis A: Chemical 298.1-2, 2009, 94-98, 5 pages.

Harvey et al., "A new chromone and flavone synthesis and its utilization for the synthesis of potentially antitumorigenic polycyclic chromones and flavones." The Journal of Organic Chemistry 55.25, 1990, 6161-6166, 6 pages.

He et al., "Highly enantioselective azadiene Diels-Alder reactions catalyzed by chiral N-heterocyclic carbenes." Journal of the American Chemical Society 128.26, 2006, 8418-8420, 3 pages.

Hopkinson et al., "An overview of N-heterocyclic carbenes." Nature 510.7506, 2014, 485-496, 12 pages.

Hostetler et al., "Flavones: Food sources, bioavailability, metabolism, and bioactivity." Advances in Nutrition 8.3, 2017, 423-435, 13 pages.

Huynh et al., "Syntheses and catalytic activities of Pd (II) dicarbene and hetero-dicarbene complexes." Journal of Organometallic Chemistry 696.21, 2011, 3369-3375, 7 pages.

Ibrahim et al., "Efficient N-heterocyclic carbene palladium (II) catalysts for carbonylative Suzuki-Miyaura coupling reactions leading to aryl ketones and diketones." Journal of Organometallic Chemistry 859, 2018, 44-51, 21 pages.

Ibrahim et al., "Novel (N-heterocyclic carbene) Pd (pyridine) Br2 complexes for carbonylative Sonogashira coupling reactions: Catalytic efficiency and scope for arylalkynes, alkylalkynes and dialkynes." Applied Organometallic Chemistry 32.4, 4280, 2018, 11 pages.

Ibrahim et al., "Synthesis, crystal structures and catalytic activities of new palladium (II)—bis (oxazoline) complexes." Transition Metal Chemistry 41.7, 2016, 739-749.

Ishiyama et al., "Synthesis of unsymmetrical biaryl ketones via palladium-catalyzed carbonylative cross-coupling reaction of arylboronic acids with iodoarenes." Tetrahedron letters 34.47, 1993, 7595-7598, 4 pages.

Islam et al., "Potent α-glucosidase and protein tyrosine phosphatase IB inhibitors from Artemisia capillaris." Archives of pharmacal research 36.5, 2013, 542-552, 11 pages.

Ismail et al., "Synthesis and biological evaluation of some novel 4H-benzopyran-4-one derivatives as nonsteroidal antiestrogens." European journal of medicinal chemistry 36.3, 2001, 243-253, 11 pages.

Jagadeesan et al., "The nature of Pd-carbene and Pd-halogen bonds in (bisNHC) PdX 2 type catalysts: insights from density functional theory," RSC advances 5.98, 2015, 80661-80667, 7 pages.

Kabalka et al., "Microwave-assisted synthesis of functionalized flavones and chromones." Tetrahedron Letters 46.37, 2005, 6315-6317, 3 pages.

Kang et al., "Pd (0)—Cu (I)-catalyzed cross-coupling of alkynylsilanes with triarylantimony (V) diacetates." Journal of the Chemical Society, Perkin Transactions 1 7 (2001): 736-739, 4 pages.

Ker et al., "Chromones as a privileged scaffold in drug discovery: A review." European journal of medicinal chemistry 78, 2014, 340-374, 35 pages.

Ketike et al., "Carbonylative Suzuki-Miyaura cross-coupling over Pd NPs/Rice-Husk carbon-silica solid catalyst: Effect of 1, 4-dioxane solvent," ChemistrySelect 3.25, 2018, 7164-7169, 6 pages.

Kim et al., "Unified approach to (thio) chromenones via one-pot Friedel-Crafts acylation/cyclization: Distinctive mechanistic pathways of B-chlorovinyl ketones." Organic letters 19.2, 2017, 312-315, 4 pages.

Kobayash et al., "Carbonylation of organic halides in the presence of terminal acetylenes; novel acetylenic ketone synthesis." Journal of the Chemical Society, Chemical Communications 7, 1981, 333-334, 2 pages.

Kostyukovich et al., "In situ transformations of Pd/NHC complexes with N-heterocyclic carbene ligands of different nature into colloidal Pd nanoparticles." Inorganic Chemistry Frontiers 6.2, 2019, 482-492, 11 pages.

Kumar et al., "Stereoelectronic Profiling of Expanded-Ring N-Heterocyclic Carbenes." Inorganic chemistiy 58.11, 2019, 7545-7553, 9 pages.

Lee et al., "Carbonylative Coupling of 4, 4'-Diiodobiphenyl Catalyzed by Pd (NHC) Complex.", 2013, 4 pages.

Liang et al., "Pd-catalyzed copper-free carbonylative Sonogashira reaction of aryl iodides with alkynes for the synthesis of alkynyl ketones and flavones by using water as a solvent." The Journal of organic chemistry 70.15, 2005, 6097-6100, 4 pages.

Liu et al., "Construction of the flavones and aurones through regioselective carbonylative annulation of 2-bromophenols and terminal alkynes." Tetrahedron Letters 54.14, 2013, 1802-1807, 6 pages.

Liu et al., "Magnetically separable Pd catalyst for carbonylative sonogashira coupling reactions for the synthesis of α, β-alkynyl ketones." Organic letters 10.18, 2008, 3933-3936, 4 pages.

Ma et al., "N-Heterocyclic carbene-stabilized palladium complexes as organometallic catalysts for bioorthogonal cross-coupling reactions." The Journal of organic chemistry 79.18, 2014, 8652-8658, 7 pages.

Maiti et al., "Synthesis and cancer chemopreventive activity of zapotin, a natural product from Casimiroa edulis." Journal of medicinal chemistry 50.2, 2007, 350-355, 6 pages.

Mansour et al., "Novel and efficient bridged bis (N-heterocyclic carbene) palladium (II) catalysts for selective carbonylative Suzuki-Miyaura coupling reactions to biaryl ketones and biaryl diketones." Applied Organometallic Chemistry 34.6, e5636, 2020, 20 pages.

Miao et al., "Regiospecific carbonylative annulation of iodophenol acetates and acetylenes to construct the flavones by a new catalyst of palladium-thiourea-dppp complex." Organic letters 2.12, 2000, 1765-1768, 4 pages.

Mingji et al., "A novel thiourea ligand applied in the Pd-catalyzed Heck, Suzuki and Suzuki carbonylative reactions." Advanced Synthesis & Catalysis 346.13-15, 2004, 1669-1673, 5 pages.

Mohamed et al., "Carbonylative sonogashira coupling of terminal alkynes with aqueous ammonia." Organic letters 5.17 (2003): 3057-3060, 4 pages.

Mohapatra et al., "Michael Addition of Imidazole to α, β-Unsaturated Carbonyl/Cyano Compound." Open Chemistry Journal 5.1, 2018, 14 pages.

Morimoto et al., "Insect antifeedant activity of flavones and chromones against Spodoptera litura." Journal of agricultural and food chemistry 51.2, 2003, 389-393, 5 pages.

Muskawar et al., "NHC-metal complexes based on benzimidazolium moiety for chemical transformation: 1st Cancer Update." Arabian Journal of Chemistry 9, 2016, S1765-S1778, 14 pages.

Musthafa et al., "Microwave-assisted solvent-free synthesis of biologically active novel heterocycles from 3-formylchromones." Medicinal Chemistry Research 20.9, 2011,1473-1481, 9 pages.

Nelson et al., "Quantifying and understanding the electronic properties of N-heterocyclic carbenes." Chemical Society Reviews 42.16, 2013, 6723-6753, 31 pages.

Netzer et al., "The actual role of sodium cromoglycate in the treatment of asthma—a critical review." Sleep and Breathing 16.4, 1027-1032, 2012, 6 pages.

Nguyen et al., "Postmodification Approach to Charge-Tagged 1, 2, 4-Triazole-Derived NHC Palladium (II) Complexes and Their Applications." Organometallics 36.12, 2017, 2345-2353, 9 pages.

Niu et al., "Preparation of Recoverable Pd Catalysts for Carbonylative Cross-Coupling and Hydrogenation Reactions." ChemCatChem 5.1 (2013): 349-354, 6 pages.

Niu et al., "Stabilizing Pd II on hollow magnetic mesoporous spheres: a highly active and recyclable catalyst for carbonylative cross-coupling and Suzuki coupling reactions." New Journal of Chemistry 38.4, 2014, 1471-1476, 6 pages.

O'Keefe et al., "Carbonylative Cross-Coupling of ortho-Disubstituted Aryl Iodides. Convenient Synthesis of Sterically Hindered Aryl Ketones." Organic letters 10.22, 2008, 5301-5304, 4 pages.

Park et al., "Pd-catalyzed carbonylative reactions of aryl iodides and alkynyl carboxylic acids via decarboxylative couplings." Organic Letters 13.5, 2011, 944-947, 4 pages.

(56) References Cited

OTHER PUBLICATIONS

Qi et al., "Selective palladium-catalyzed carbonylative synthesis of aurones with formic acid as the CO source." RSC advances 6.67,2016, 62810-62813, 4 pages.
Rajabi et al., "An Efficient Palladium N-Heterocyclic Carbene Catalyst Allowing the Suzuki-Miyaura Cross-Coupling of Aryl Chlorides and Arylboronic Acids at Room Temperature in Aqueous Solution," Advanced Synthesis & Catalysis 356.8, 2014, 1873-1877, 5 pa.
Rueping et al., "A review of new developments in the Friedel-Crafts alkylation—From green chemistry to asymmetric catalysis." Beilstein journal of organic chemistry 6.1, 2010, 24 pages.
Sakaguchi et al., "Chiral Palladium (II) Complexes Possessing a Tridentate N-Heterocyclic Carbene Amidate Alkoxide Ligand: Access to Oxygen-Bridging Dimer Structures." Angewandte Chemie International Edition 47.48, 2008, 9326-9329, 4 pages.
Sartori et al., Advances in Friedel-Crafts Acy/ation Reactions: Catalytic and Green Processes book 1st Edition, 2009, 222 pages.
Schmid et al., "Mixed phosphine/N-heterocyclic carbene palladium complexes: Synthesis, characterization and catalytic use in aqueous Suzuki-Miyaura reactions." Dalton Transactions 42.20, 2013, 7345-7353, 9 pages.
Tambade et al., "Copper-Catalyzed, Palladium-Free Carbonylative Sonogashira Coupling Reaction of Aliphatic and Aromatic Alkynes with Iodoaryls." Synlett 2008.06, 2008, 886-888, 3 pages.
Tambade et al., "Phosphane-Free Palladium-Catalyzed Carbonylative Suzuki Coupling Reaction of Aryl and Heteroaryl Iodides." European Journal of Organic Chemistry 2009.18, 2009, 3022-3025, 4 pages.
Taniguchi, "Aerobic nickel-catalyzed hydroxysulfonylation of alkenes using sodium sulfinates." The Journal of organic chemistry 80.15, 2015, 7797-7802, 20 pages.
Tao et al., "Palladium complexes bearing an N-heterocyclic carbene-sulfonamide ligand for cooligomerization of ethylene and polar monomers." Journal of Polymer Science Part A: Polymer Chemistry 57.3, 2019, 474-477, 4 pages.
Taylor et al., "Metal-free Synthesis of Ynones from Acyl Chlorides and Potassium Alkynyltrifluoroborate Salts." JoVE (Journal of Visualized Experiments) 96, e52401, 2015, 9 pages.
Touj et al., "Correction: Efficient in situ N-heterocyclic carbene palladium (ii) generated from Pd (OAc) 2 catalysts for carbonylative Suzuki coupling reactions of arylboronic acids with 2-bromopyridine under inert conditions leading to unsymmetrical arylpyridine ketones: synthesis, characterization and cytotoxic activities." RSC Advances 9.2, 2019, 16 pages.
Wang et al., "Carbonylative Suzuki cross-coupling reaction catalyzed by bimetallic Pd—Pt nanodendrites under ambient CO pressure." Catalysis Communications 101, 2017, 10-14, 21 pages.
Wang et al., "Cross-linked polymer supported palladium catalyzed carbonylative Sonogashira coupling reaction in water," Tetrahedron letters 52.14, 2011, 1587-1591, 5 pages.
Wang et al., "N-heterocyclic carbene-palladium (II) complexes with benzoxazole or benzothiazole ligands: Synthesis, characterization, and application to Suzuki-Miyaura cross-coupling reaction." Journal of Organometallic Chemistry 804, 2016, 73-79, 24 page.
Wu et al., "A General Palladium-Catalyzed Carbonylative Sonogashira Coupling of Aryl Triflates." Chemistry—A European Journal 17.1, 2011, 106-110, 5 pages.
Wu et al., "Palladium-Catalyzed Carbonylation Reaction of Aryl Bromides with 2-Hydroxyacetophenones to Form Flavones." Chemistry—A European Journal 18.40, 2012, 12595-12598, 5 pages.

Wu et al., "Palladium-catalyzed carbonylative coupling of benzyl chlorides with terminal alkynes to give 1, 4-diaryl-3-butyn-2-ones and related furanones." Organic & Biomolecular Chemistry 9.23, 2011, 8003-8005, 3 pages.
Xu et al., "Divergent synthesis of flavones and aurones via base-controlled regioselective palladium catalyzed carbonylative cyclization," Molecular Catalysis 452, 2018, 264-270, 7 pages.
Xue et al., "Pd-carbene catalyzed carbonylation reactions of aryl iodides." Dalton Transactions 40.29, 2011, 7632-7638, 7 pages.
Yang et al., "Pd catalyzed couplings of "superactive esters" and terminal alkynes: Application to flavones and y-benzopyranones construction." Journal of Molecular Catalysis A: Chemical 426, 2017, 24-29, 6 pages.
Yang et al., "Synthesis of chromones via palladium-catalyzed ligand-free cyclocarbonylation of o-iodophenols with terminal acetylenes in phosphonium salt ionic liquids." The Journal of organic chemistry 75.3, 2010, 948-950, 3 pages.
Yaşar et al., "Microwave-Assisted Synthesis of 4'-Azaflavones and Their N-Alkyl Derivatives with Biological Activities." Chemistry & biodiversity 5.5, 2008, 830-838, 9 pages.
Yoshida et al., "A concise total synthesis of biologically active frutinones via tributylphosphine-catalyzed tandem acyl transfer-cyclization," Tetrahedron 70.21, 2014, 3452-3458, 7 pages.
Zhang et al., "Aryl-palladium-NHC complex: efficient phosphine-free catalyst precursors for the carbonylation of aryl iodides with amines or alkynes." Organic & Biomolecular Chemistry 12.47, 2014, 9702-9706, 5 pages.
Zhang et al., "Chiral linker-bridged bis-N-heterocyclic carbenes: design, synthesis, palladium complexes, and catalytic properties." Dalton Transactions 45.29, 2016, 11699-11709, 14 pages.
Zhang et al., "Enantioselective formal [4+ 2] annulation of ortho-quinone methides with orthohydroxyphenyl α, β-unsaturated compounds." The Journal of organic chemistry 83.17, 2018, 10175-10185, 11 pages.
Zhao et al., "C—H functionalization via remote hydride elimination: Palladium catalyzed dehydrogenation of ortho-acyl phenols to flavonoids." Organic letters 19.5, 2017, 976-979, 4 pages.
Zhao et al., "Synthesis and insecticidal activity of chromanone and chromone analogues of diacylhydrazines." Bioorganic & medicinal chemistry 15.5, 2007, 1888-1895, 8 pages.
Zheng et al., "Highly efficient N-Heterocyclic carbene-palladium complex-catalyzed multicomponent carbonylative Suzuki reaction: novel practical synthesis of unsymmetric aryl ketones." Applied Organometallic Chemistry 21.9, 2007, 772-776, 5 pages.
Zhiping et al., "Synthesis of propylene carbonate from alcoholysis of urea catalyzed by modified hydroxyapatites." Chinese Journal of Catalysis 31.4, 2010, 3 pages.
Zhiping et al., "Transition-Metal-Catalyzed Carbonylative Synthesis and Functionalization of Heterocycles." Chinese Journal of Organic Chemistry 39.3, 2019, 573-590, 18 pages.
Zhong et al., "An efficient synthesis of 4-chromanones." Tetrahedron letters 52.38, 2011, 4824-4826, 3 pages.
Zhou et al., "Synthesis of indoles through Palladium-catalyzed three-component reaction of aryl iodides, alkynes, and diaziridinone." Organic letters 20.20, 2018, 6440-6443, 4 pages.
Zhu et al., "Highly efficient synthesis of flavones via Pd/C-catalyzed cyclocarbonylation of 2-iodophenol with terminal acetylenes." Catalysis Science & Technology 6.9, 2016, 2905-2909,4 pages.
U.S. Appl. No. 17/071,381, filed Oct. 15, 2020, Ali et al.
U.S. Appl. No. 17/071,713, filed Oct. 15, 2020, Ali et al.
Avery et al., "Use of a silicon carbide multi-well plate in conjunction with micro wave heating for rapid ligand synthesis, formation of palladium complexes, and catalyst screening in a Suzuki coupling," Tetrahedron Letters 50.24, 2009, 2851-2853, 3 pages.

C1

C2

C3

700

800

900

+ CO

C1, C2, or C3
───────────→
Et$_2$NH, DMF
100 psi, 110°C

SELECTIVE CYCLOCARBONYLATIVE COUPLING OF 2-IODOPHENOLS WITH TERMINAL ALKYNES CATALYZED BY BRIDGED BIS(NHC)PD(II)BR₂ CATALYSTS

TECHNICAL FIELD

This document relates to palladium-carbenes complexes and cyclocarbonylative Sonogashira cross-coupling reactions.

BACKGROUND

Chromones and aurones are useful precursors to pharmacological compounds, and new and efficient methods and catalysts for producing chromones and aurones are needed.

SUMMARY

This disclosure describes palladium catalysts, methods of synthesizing palladium-carbene catalysts, and methods of producing chromones and aurones using palladium-N-heterocyclic carbene (NHC) catalysts.

In some implementations, a compound of Formula C3 has the following structure:

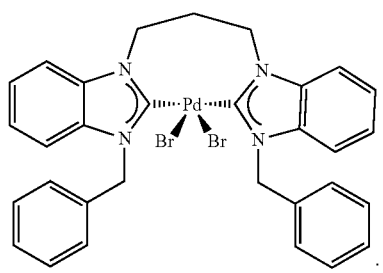

In some implementations, a method of synthesizing a palladium catalyst includes reacting a benzimidazole with a halogenated hydrocarbon in the presence of a base and acetonitrile to produce an alkyl-1H-benzo[d]imidazole, reacting the alkyl-1H-benzo[d]imidazole with a halogenated crosslinking chain to produce a bridged N-heterocyclic carbene salt precursor, and reacting the bridged N-heterocyclic carbene with palladium acetate.

In some implementations, a method of synthesizing chromones or aurones includes reacting a 2-iodophenol and an aryl alkyne in the presence of a palladium catalyst, wherein the palladium catalyst includes at least one of Formula C1, Formula C2, or Formula C3, where Formula C1 has the structure

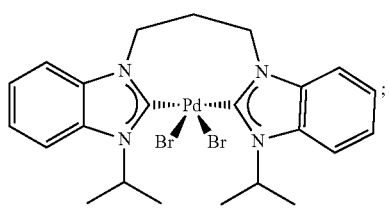

Formula C2 has the structure

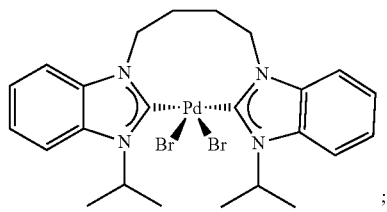

and
Formula C3 has the structure

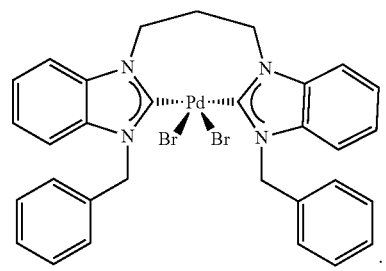

In some implementations, a method of synthesizing chromones or aurones includes reacting a 2-iodophenol and an alkyl alkyne in the presence of a palladium catalyst, wherein the palladium catalyst includes at least one of Formula C1, Formula C2, or Formula C3, where Formula C1 is

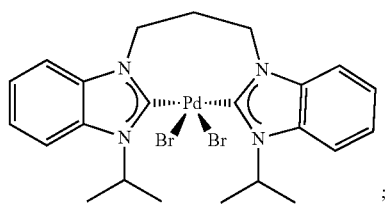

Formula (C2) is

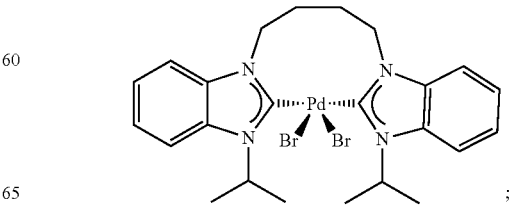

and
Formula (C3) is

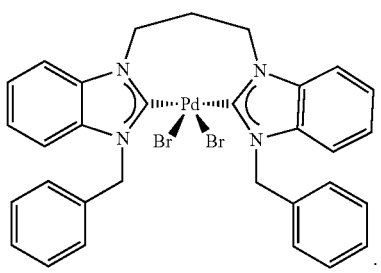

The details of one or more implementations of the disclosure are set forth in the accompanying drawings and the description that follows. Other features, objects, and advantages of the disclosure will be apparent from the description and drawings, and from the claims.

DESCRIPTION OF DRAWINGS

Like reference symbols in the various drawings indicate like elements.

DETAILED DESCRIPTION

Reference will now be made in detail to certain embodiments of the disclosed subject matter, examples of which are illustrated in part in the accompanying drawings. While the disclosed subject matter will be described in conjunction with the enumerated claims, it will be understood that the exemplified subject matter is not intended to limit the claims to the disclosed subject matter.

Provided in this disclosure, in part, are palladium catalysts, methods of synthesizing palladium catalysts, and methods of producing chromones and aurones using palladium bridged bis(NHCs) catalysts.

In some implementations, a catalyst containing palladium is complexed with one or more N-heterocyclic carbenes (NHC). For example, palladium can be complexed with benzimidazole. The palladium-NHC complex (Pd—NHC) can be used to catalyze Sonogashira reactions.

Figure 1:
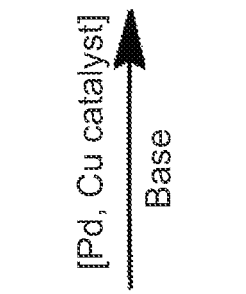
FIG. 1 shows an example of Sonogashira cross-coupling reaction.
Figure 1:
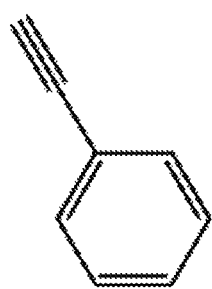
Figure 1:
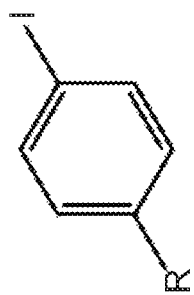

Sonogashira reactions can be exemplified by three types of reactions. In a first type of Sonogashira cross-coupling reaction, a carbon-carbon bond is formed between a terminal alkyne and an aryl or vinyl halide, resulting in an aryl alkyne. This type of reaction uses both a palladium catalyst and a copper catalyst. FIG. 1 shows an example of this type of a Sonogashira cross-coupling reaction.

Figure 2:
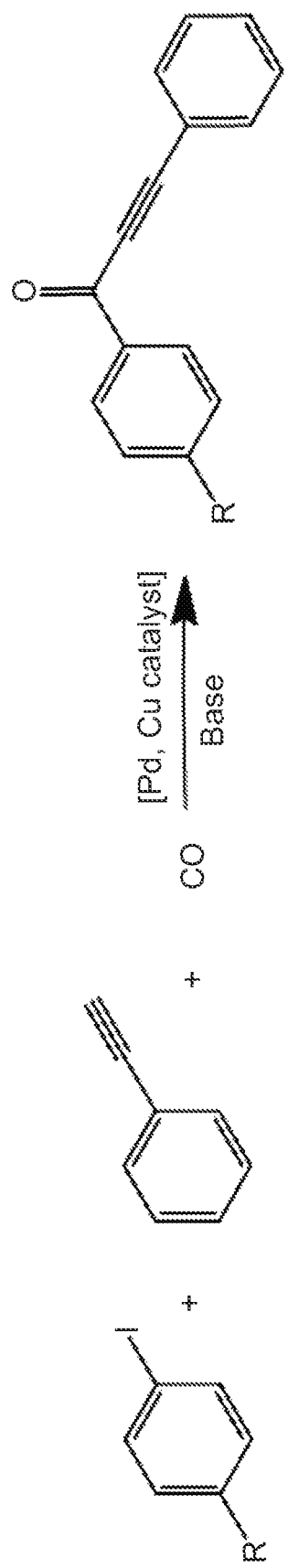
FIG. 2 shows an example of carbonylative Sonogashira cross-coupling reaction.

In a carbonylative Sonogashira cross-coupling reaction, a carbonyl-carbon bond is formed between a terminal alkyne and an aryl halide under carbon monoxide, resulting in an alkynone. Alkynones are known to be bioactive. Carbonylative Sonogashira cross-coupling reactions employ a palladium catalyst and a copper co-catalyst in the presence of carbon monoxide (CO). FIG. 2 shows an example of a carbonylative Sonogashira cross-coupling reaction.

Figure 3:
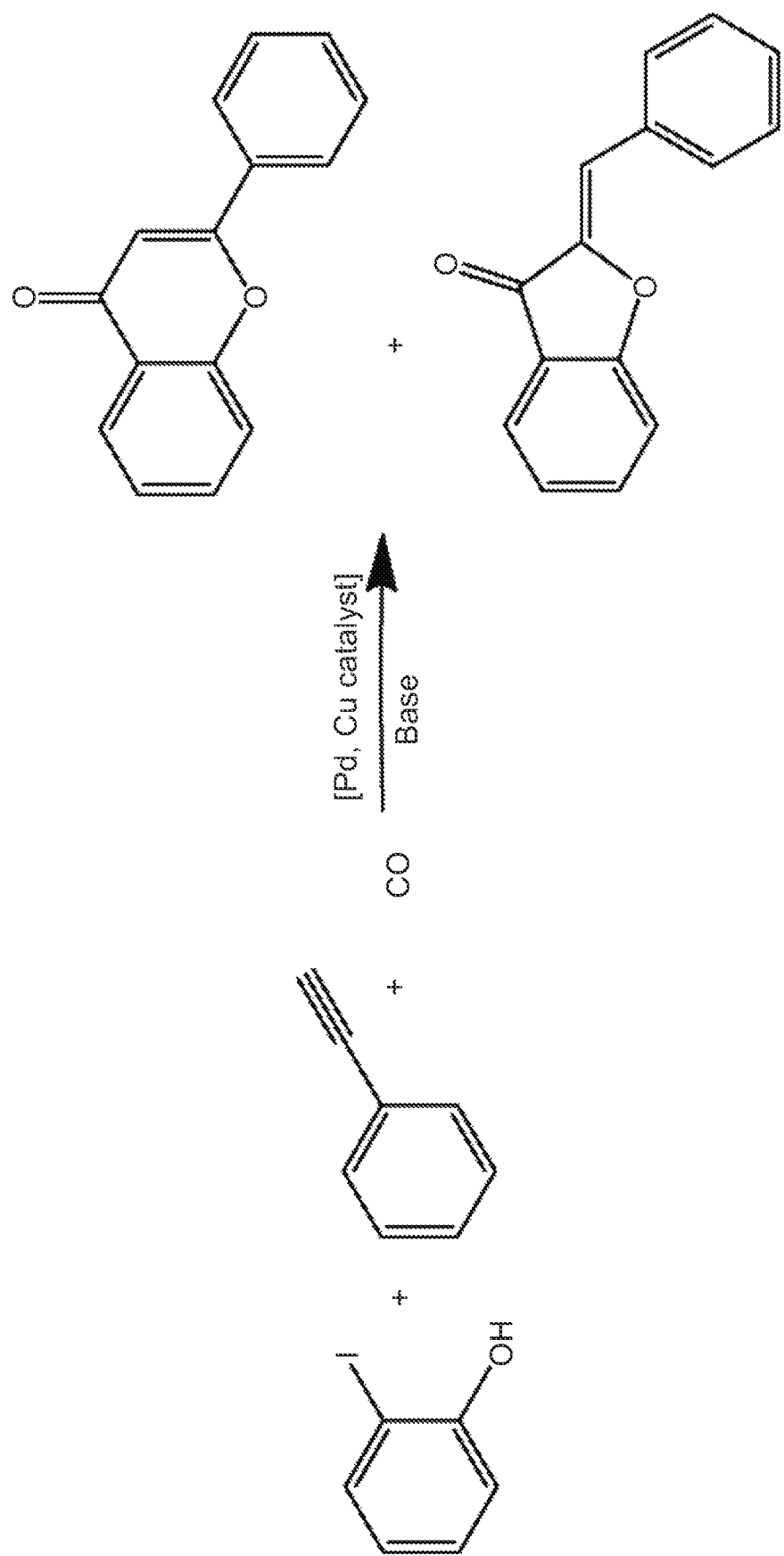
FIG. 3 shows an example of cyclocarbonylative Sonogashira cross-coupling reaction.
Figure 4:
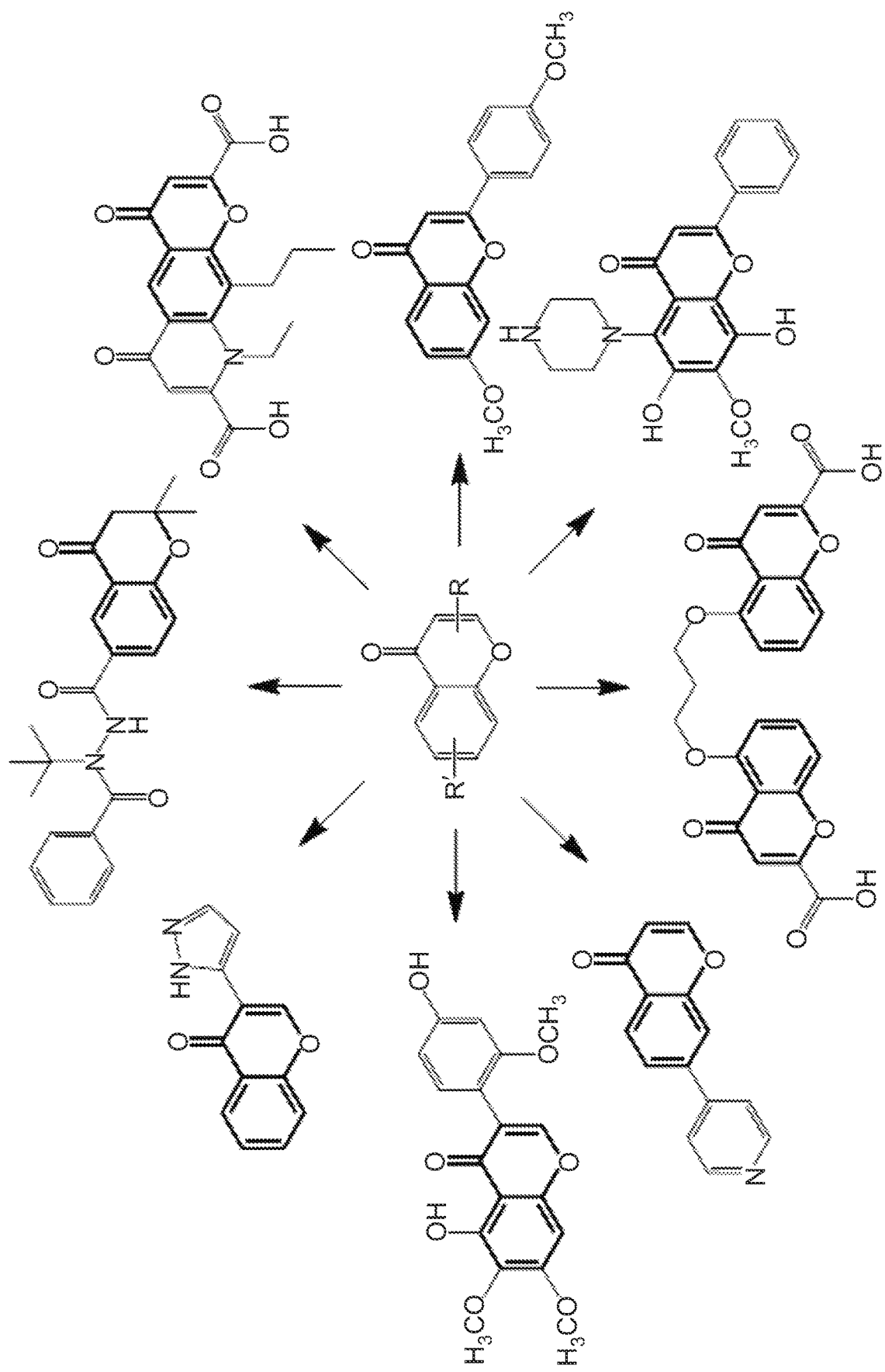
FIG. 4 shows examples of chromones.

In a cyclocarbonylative Sonogashira cross-coupling reaction, carbonylative coupling reactions occur in the presence of carbon monoxide to form carbonyl-carbon bonds. The reaction products include five- or six-membered ring ketones. Cyclocarbonylative Sonogashira cross-coupling reactions employ palladium catalysts, and can employ copper co-catalysts. The carbonyl-carbon bonds are formed via cyclocarbonylative coupling reactions between a terminal alkyne and a halogenated phenol. Five-membered ring products of this reaction are referred to as aurones, and six-membered ring products are referred to as chromones. FIG. 3 shows an example of a cyclocarbonylative Sonogashira cross-coupling reaction that yields an aurone or a chromone. Chromones and aurones have industrial and pharmaceutical applications, for example as precursor compounds. FIG. 4 illustrates a number of different chromones, which have uses in anticancer, anti-microbial, anti-inflammatory, and anti-viral applications, among others. Accordingly, there is a need for new chromones and new methods of producing chromones.

Pd—NHC complexes can be used for Sonogashira cross-coupling and carbonylative Sonogashira cross-coupling reactions. However, bridged bis(NHC)Pd(II)Br$_2$ complexes that include N-heterocyclic carbenes (NHCs) have not previously been used for cyclocarbonylative Sonogashira cross-coupling reactions. The bridged bis(NHC)Pd(II)Br$_2$ catalysts described herein can be used in a cyclocarbonylative Sonogashira cross-coupling reaction to yield chromones and aurones. Advantageously, these catalysts can be used for cyclocarbonylative Sonogashira cross-coupling reactions in the absence of phosphines or any other ligands or co-catalysts.

Figure 5:
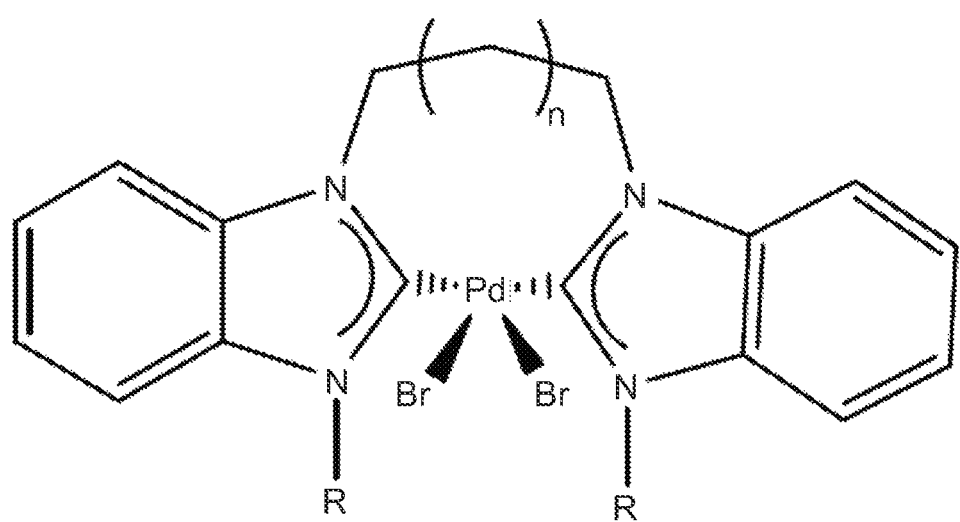
FIG. 5 shows a bridged bis(N-Heterocyclic Carbene) palladium(II) [bis(NHC)Pd(II)] catalyst.

In some implementations, the catalyst for cyclocarbonylative Sonogashira cross-coupling reaction is a bridged palladium complex shown in FIG. 5. The catalyst contains a bridged palladium with specific stereochemistry. As shown by X-ray diffraction analysis, the Pd(II) complexes shown in FIG. 5 can have distorted square planar geometries around the center palladium atom.

The alkyl bridge between N-heterocyclic carbene units can vary in length. The alkyl bridge is shown in FIG. 5 with n number of repeating methylene units. In some implementations, n is 1, 2, or 3.

Figure 6:
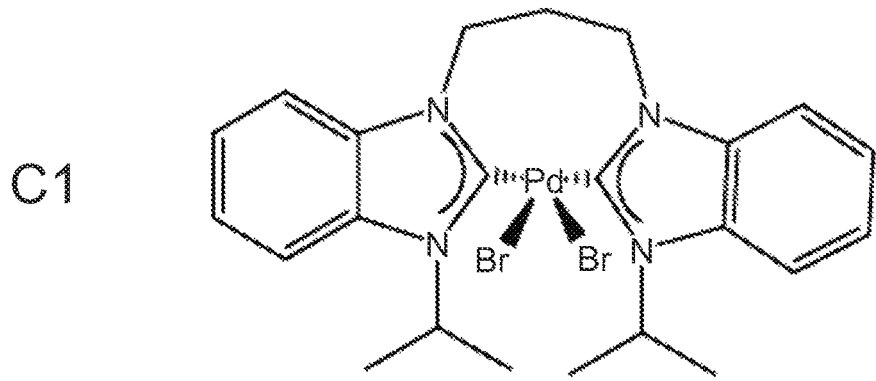
FIG. 6 shows the structure of three bis(NHC)Pd(II)Br$_2$ catalysts.
Figure 6:
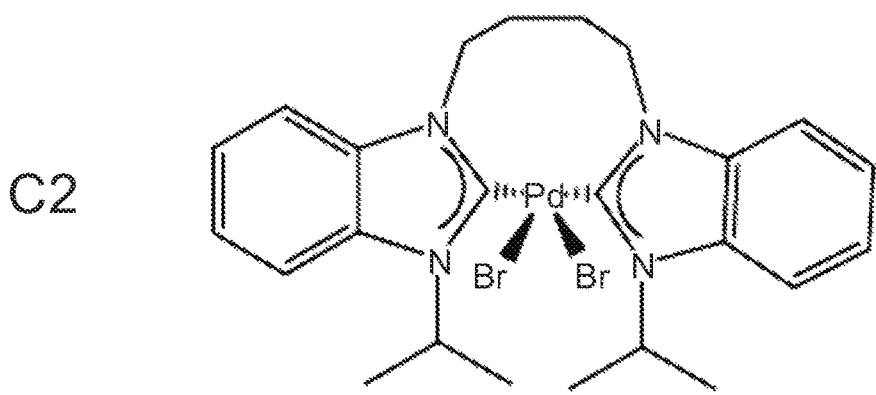
Figure 6:
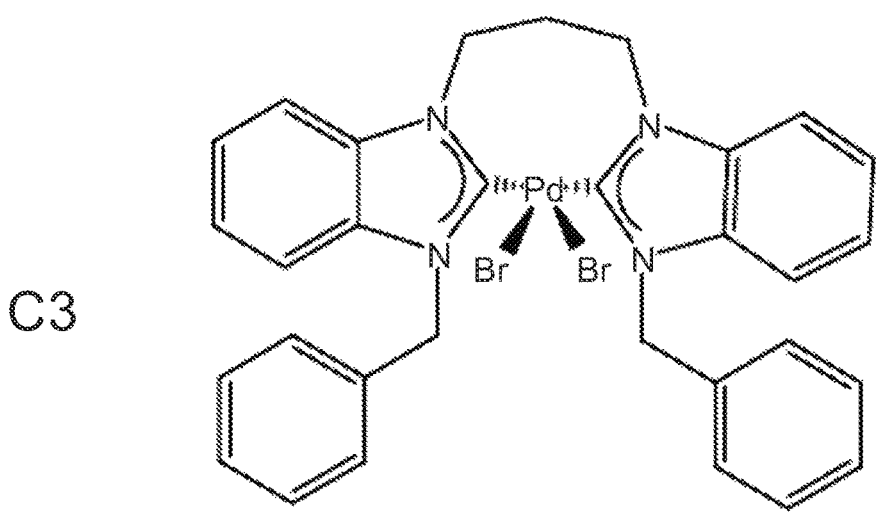

The N-heterocyclic carbenes can be functionalized with a functional group R. In some implementations, R is a straight or branched alkyl group, for example —CH(CH$_3$)$_2$. In some implementations, R includes a carbon ring structure or aromatic group, for example —CH$_2$Ph. The functional group R can alter the steric hindrance around the palladium center and alter the functionality of the catalyst. FIG. 6 shows the structure of three palladium catalysts C1, C2, and C3, which were used in cyclocarbonylative Sonogashira cross-coupling reactions. The synthesis of these catalysts is discussed in Examples 1-3.

Catalysts C1, C2, and C3 are stable complexes. For example, C1, C2, and C3 are stable at temperatures as high as 120° C. These catalysts are efficient and selective. In addition, the catalysts have low loading requirements, wide substrate applications, and high yields. The geometry and configuration of C1, C2, and C3 yields a specific catalytic activity that is advantageous for cyclocarbonylative Sonogashira cross-coupling reactions. Further, the regioselectivity of the catalysts can be controlled using specific solvents and a base, for example dimethyl formamide (DMF) as a solvent and diethylamine (Et$_2$NH) as a base. The selectivity of the catalysts is shown in Table 6. In addition, the catalysts can be used with catalyst loading as small as 0.50 mol %, and in the absence of phosphines or any co-ligands.

Figure 7:
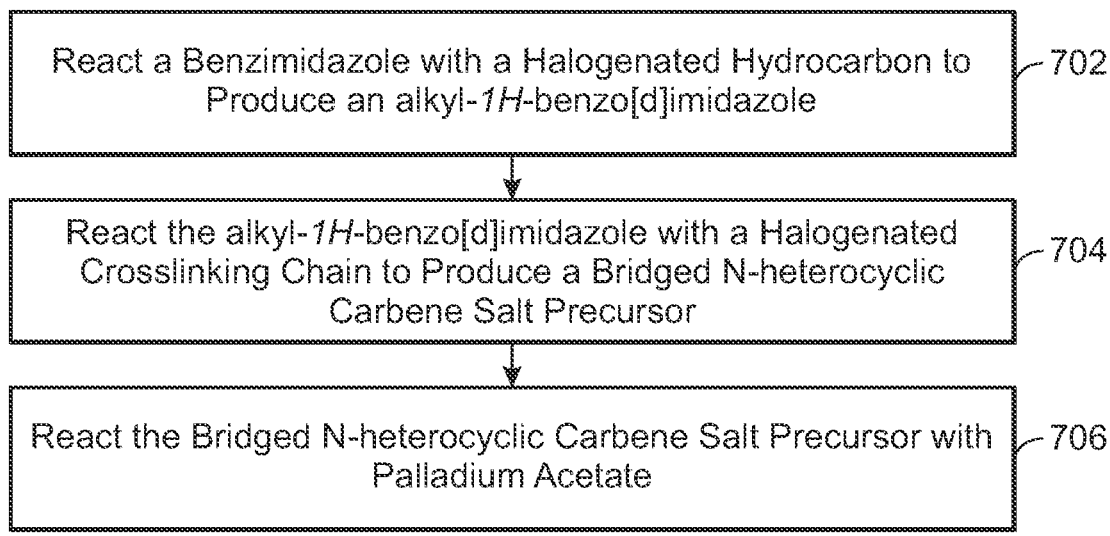
FIG. 7 is a flow chart of an example method of synthesizing a palladium bridged bis(NHCs) catalyst.

FIG. 7 is a flow chart of an example method 700 of synthesizing palladium catalysts C1, C2, and C3. At 702, a benzimidazole is reacted with a halogenated hydrocarbon to produce an alkyl-1H-benzo[d]imidazole. At 704, the alkyl-1H-benzo[d]imidazole is reacted with a halogenated cross-linking chain to produce a bridged N-heterocyclic carbene salt precursor. At 706, the bridged N-heterocyclic carbene salt precursor is reacted with acetylated palladium.

Figure 8:
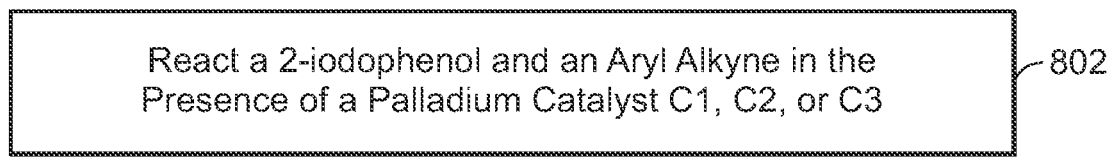
FIG. 8 is a flow chart of an example method of synthesizing chromones or aurones.

FIG. 8 is a flow chart of an example method 800 of synthesizing chromones or aurones. At 802, a 2-iodophenol is reacted with an aryl alkyne in the presence of a palladium catalyst C1, C2, or C3.

Figure 9:
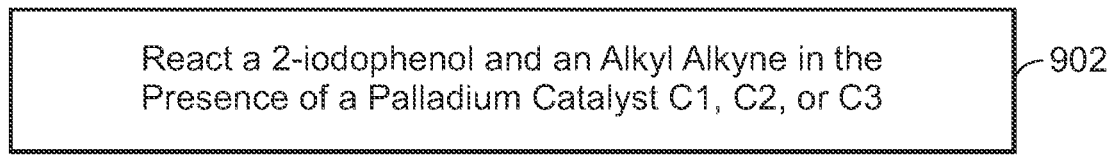
FIG. 9 is a flow chart of a second example method of synthesizing chromones or aurones.

FIG. 9 is a flow chart of a second example method 900 of synthesizing chromones or aurones. At 902, a 2-iodophenol is reacted with an alkyl alkyne in the presence of a palladium catalyst C1, C2, or C3.

Example 1: Synthesis of Benzimidazole Precursors

Figure 10:
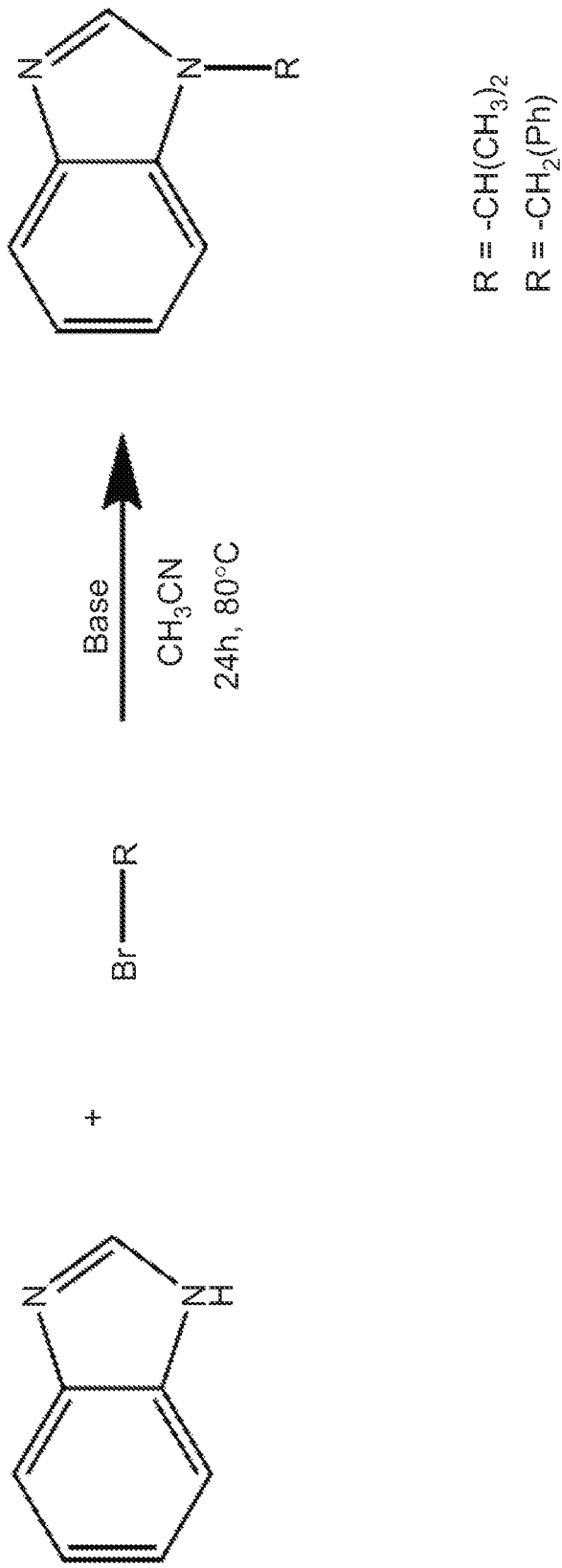
FIG. 10 shows an example of a reaction between a benzimidazole and an alkyl halide.

Bis-NHC—Pd(II) catalysts as shown in FIG. 5 were synthesized using alkylated benzimidazole precursors. FIG. 10 shows an example of a reaction between a benzimidazole with a halogenated alkyl group in the presence of base and acetonitrile to generate alkyl-1H-benzo[d]imidazoles. The functional group R can include branched alkyl or aromatic groups. For example, R can be —CH(CH$_3$)$_2$ or —CH$_2$Ph.

The synthesis of benzimidazole precursors is described herein. A dry and clean round bottom flask was charged with benzimidazole (10.0 mmol), excess amount of alkyl bromide (12.2 mmol), an appropriate base (20.0 mmol), and 1.00 mmol of tetrabutylammonium bromide (TBAB). For the synthesis of 1-isopropyl-1H-benzo[d]imidazole, the alkyl bromide is 2-bromopropane and the base is potassium hydroxide. For the synthesis of 1-benzyl-1H-benzo[d]imidazole, the alkyl bromide is benzyl bromide and the base is cesium carbonate. 100 mL of acetonitrile was used to dissolve the prepared mixture with continuous stirring at 80° C. for 24 h. Thin layer chromatography (TLC) (1/1=hexane/ethyl acetate) was used for monitoring the reaction until no free benzimidazole was observed. After the completion of the reactions, the solvents were removed under vacuum by rotary evaporator. The oily products were collected as residues, and the purification of the products was conducted by extraction twice with 30 mL ethyl acetate and 20 mL distilled water. The aqueous layers were separated then washed with ethyl acetate. The separated organic layers were dried and washed several times with n-hexane.

The synthesized compounds were analyzed by $^1$H NMR (nuclear magnetic resonance) analysis and $^{13}$C{$^1$H} NMR analysis. For the NMR analyses, 's' denotes a singlet, 'd' denotes a doublet, 'dd' denotes a doublet of doublets, 't' denotes a triplet, 'q' denotes a quartet, 'qui' denotes a quintet, and 'sept' denotes a septet. The coupling constant is given as J.

Synthesis of 1-isopropyl-1H-benzo[d]imidazole resulted in a 77% yield by mass of a sticky brown oil. $^1$H NMR analysis (400 MHz, CDCl$_3$) yielded the following spectra in δ (ppm): 7.85 (s, 1H, NCHN), 7.64-7.62 (1H, m, Ar—H), 7.25-7.22 (1H, m, Ar—H), 7.11-7.08 (2H, m, Ar—H), 4.42 (1H, sept, $^3$J=6.76 Hz, NCH), 1.40 (6H, d, $^3$J=6.76 Hz, NC(CH$_3$)$_2$).

$^{13}$C{$^1$H} NMR analysis (500 MHz, CDCl$_3$) yielded the following spectra in δ (ppm): 143.5 (NCN), 139.8, 132.7, 122.1, 121.5, 119.8, 109.7, (Ar—H), 47.2 (NCH), 22.02 [NC(CH$_3$)$_2$].

The theoretical composition calculated for this compound (C$_{10}$H$_{12}$N$_2$, molecular weight 160) is 74.97% carbon by mass, 7.55% hydrogen by mass, and 17.48% nitrogen by mass. Elemental analysis found 74.84% carbon by mass; 7.23% hydrogen by mass; and 17.23% nitrogen by mass.

Synthesis of 1-benzyl-1H-benzo[d]imidazole resulted in an 87% yield by mass of a light yellow solid. $^1$H NMR analysis (500 MHz, CDCl$_3$) yielded the following spectra in δ (ppm): 7.98 (1H, s, NCHN), 7.83 (1H, d, $^3$J=7.63 Hz, Ar—H), 7.34-7.24 (6H, m, Ar—H), 7.18 (2H, d, $^3$J=7.02 Hz, Ar—H), 5.36 (2H, m, NCH$_2$-Ph).

$^{13}$C{$^1$H} NMR analysis (500 MHz, CDCl$_3$) yielded the following spectra in δ (ppm): 143.1 (NCN), 135.4, 129, 128.3, 127.06, 123.1, 122.3, 120.3, 110.04 (Ar—H), 48.8 (NCH$_2$).

The theoretical composition calculated for this compound (C$_{14}$H$_{12}$N$_2$, molecular weight 208) is 80.74% carbon by mass, 5.81% hydrogen by mass, and 13.45% nitrogen by mass. Elemental analysis found 80.89% carbon by mass, 6.03% hydrogen by mass, and 13.73% nitrogen by mass.

Example 2: Synthesis of Precursors L1, L2, and L3

Figure 11:
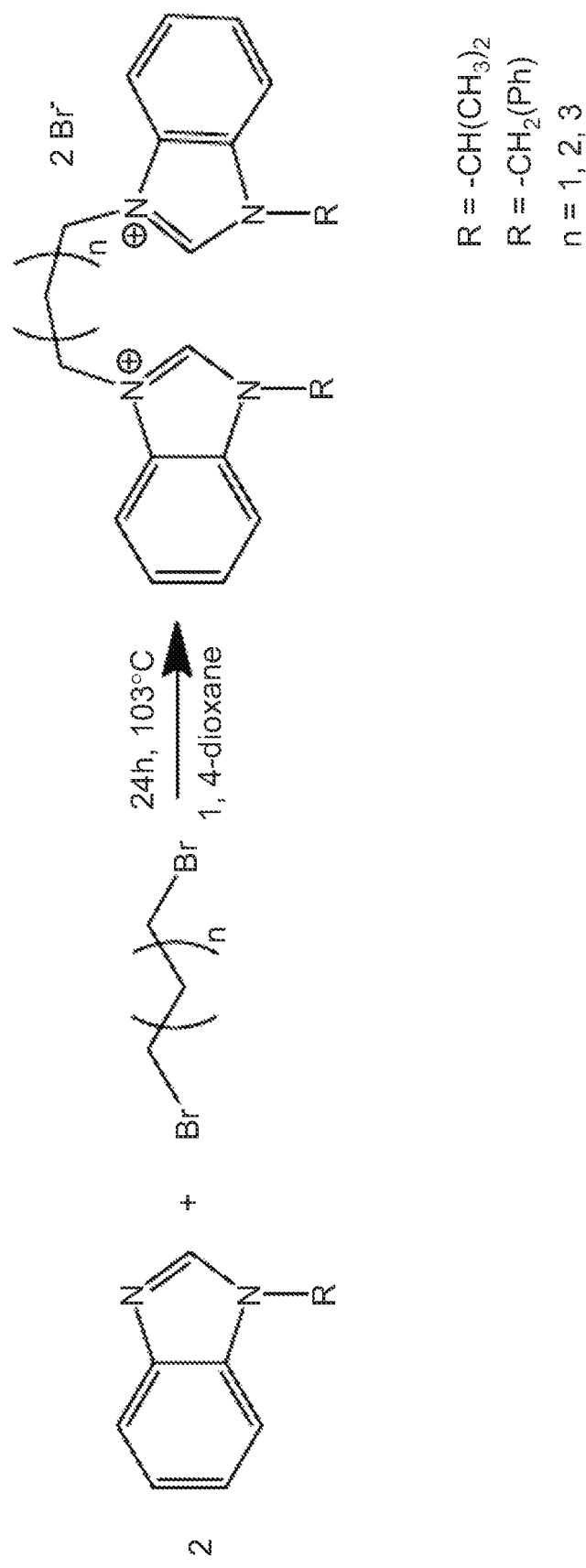
FIG. 11 shows an example of a reaction between a 1-alkyl benzimidazole produced in FIG. 10 and a halogenated crosslinking alkyl chain.

The alkylated benzimidazoles were reacted with a cross-linking halogenated alkyl chain. The alkyl chain will form the bridge of the bridged palladium catalysts. FIG. 11 shows an example reaction between the benzimidazole produced in FIG. 10 and a halogenated crosslinking alkyl chain to yield a bridged NHC salt precursor. The alkyl chain can vary in length. The alkyl chain can include n number of repeating methylene units, for example where n is 1, 2, or 3.

The 1-alkyl benzimidazoles synthesized in Example 1 (5.0 mmol) and 2.5 mmol of dibromoalkane (1,3-dibromopropane or 1,4-dibromobutane) were introduced into a dried 100 mL round bottom flask. The mixture was refluxed in 35 mL of 1,4-dioxane with stirring at 103° C. for 12 h. The products appeared as white precipitates. The products were collected by filtration and washed three times with 15 mL of 1,4-dioxane and then with 15 mL of toluene to remove any traces of the starting materials. The products were dried under vacuum then collected as a white precipitate. Characterization of the alkylene bridged N-heterocyclic dicarbene salts was conducted with different spectroscopic techniques including $^1$H NMR, $^{13}$C NMR, elemental analysis, and electrospray ionization. The resulting NHC salts are precursors L1, L2, and L3 for the palladium catalysts C1, C2, and C3.

3,3'-(propane-1,3-diyl)-bis(1-isopropyl-1H-benzo[d]imidazole-3-ium) bromide (precursor L1) was synthesized with 1-isopropyl-1H-benzo[d]imidazole and 1,3-dibromopropane as above. The synthesis resulted in a 91% yield by mass of a white solid. $^1$H NMR analysis (500 MHz, DMSO-$d_6$) yielded in the following spectra in δ (ppm): 9.83 (2H, s, NCHN), 8.15-8.11 (4H, m, Ar—H), 7.71-7.69 (2H, m, Ar—H), 5.05 (2H, sept, $^3$J=6.71 Hz, NCH), 4.67 (4H, t, $^3$J=7.01 Hz, $CH_2$), 2.67 (2H, qui, $^3$J=7.02 Hz, $CH_2$), 1.61 (12H, d, $^3$J=6.7 Hz, $NC(CH_3)_2$). $^{13}C\{^1H\}$ NMR analysis (125 MHz, DMSO) yielded the following spectra in δ (ppm): 140.7 (NCN), 131.3, 130.5, 126.7, 126.6, 114.1, 113.7, (Ar—H), 50.7 (NCH), 44.1 ($NCH_2$), 28.0 ($CH_2$), 21.6 ($NC(CH_3)_2$).

The theoretical composition of precursor L1 ($C_{23}H_{30}N_4Br_2$, molecular weight 522.3) is 52.89% carbon by mass, 5.79% hydrogen by mass, 10.73% nitrogen by mass. Elemental analysis found 52.37% carbon by mass, 5.8% hydrogen by mass, and 10.97% nitrogen by mass. Electrospray ionization analysis revealed a mass-to-charge ratio (m/z) of 442 with positive ionization and an m/z ratio of 441 with negative ionization.

3,3'-(Butane-1,4-diyl)-bis(1-isopropyl-1H-benzo[d]imidazole-3-ium) bromide (precursor L2) was synthesized with 1-isopropyl-1H-benzo[d]imidazole and 1,4-dibromobutane, as above. The synthesis resulted in a 76% yield of a white solid. $^1$H NMR analysis (500 MHz, DMSO-$d_6$) yielded the following spectra in δ (ppm): 10.05 (2H, s, NCHN), 8.13-8.11 (4H, m, Ar—H), 7.68 (4H, dd, $^3$J=6.1 Hz, $^3$J$_2$=2.75 Hz, Ar—H), 5.05 (2H, sept, $^3$J=6.71 Hz, NCH), 4.58 (4H, m, $NCH_2$), 2.04-1.99 (4H, m, $CH_2$), 1.62 [12H, d, $^3$J=6.71 Hz $(CH_3)_2$]. $^{13}C\{^1H\}$ NMR analysis (125 MHz, DMSO) yielded the following spectra in δ (ppm): 140.7 (NCN), 131.3, 130.6, 126.7, 126.6, 114.1, 113.8, (Ar—H), 50.7 (NCH), 46.3 ($NCH_2$), 25.6 ($CH_2$), 21.64 [$NC(CH_3)_2$].

The theoretical composition of precursor L2 ($C_{24}H_{32}N_4Br_2$, molecular weight 536.3) is 53.74% carbon by mass; 6.01% hydrogen by mass, and 10.45% nitrogen by mass. Elemental analysis found 52.12% carbon by mass, 5.91% hydrogen by mass, and 10.79% nitrogen by mass. Electrospray ionization analysis revealed an m/z ratio of 456 with positive ionization.

3,3'-(Propane-1,3-diyl)-bis(1-benzyl-1H-benzo[d]imidazole-3-ium) bromide (precursor L3) was synthesized with 1-benzyl-1H-benzo[d]imidazole and 1,4-dibromobutane, as above. The synthesis resulted in a 65% yield of a white solid. $^1$H NMR analysis (500 MHz, DMSO-$d_6$) yielded the following spectra in δ (ppm): 10.15 (2H, s, NCHN), 8.14 (2H, d, $^3$J$_1$=7.93 Hz, Ar—H), 7.96 (2H, d, $^3$J$_1$=7.32 Hz, Ar—H), 7.66-7.62 (4H, m, Ar—H), 7.53 (4H, d, $^3$J$_1$=7.02 Hz, Ar—H), 7.39-7.36 (4H, m, Ar—H), 5.80 (4H, s, $NCH_2Ph$), 4.62 (4H, m, $NCH_2CH_2$), 2.06 (2H, m, $CH_2$). $^{13}C\{^1H\}$ NMR analysis yielded (125 MHz, $CDCl_3$) yielded the following spectra in δ (ppm): 141.31, 132.99, 131.51, 130.77, 129.27, 129.10, 128.52, 127.26, 127.14, 114.08, 113.64 (C-arom), 51.95 ($NCH_2$), 51.37 ($NCH_2$), 22.44 2 ($CH_2CH$).

The theoretical composition of precursor L3 ($C_{31}H_{30}N_4Br_2$, molecular weight 618.4) is 60.61% carbon by mass; 4.89% hydrogen by mass, 9.06% nitrogen by mass. Elemental analysis found 60.83% carbon, 5.11% hydrogen, and 9.79% nitrogen. Electrospray ionization analysis revealed an m/z ratio of 538.5 with positive ionization.

Example 3: Synthesis of bis-NHC—Pd(II) Complexes C1, C2, and C3

Figure 12:
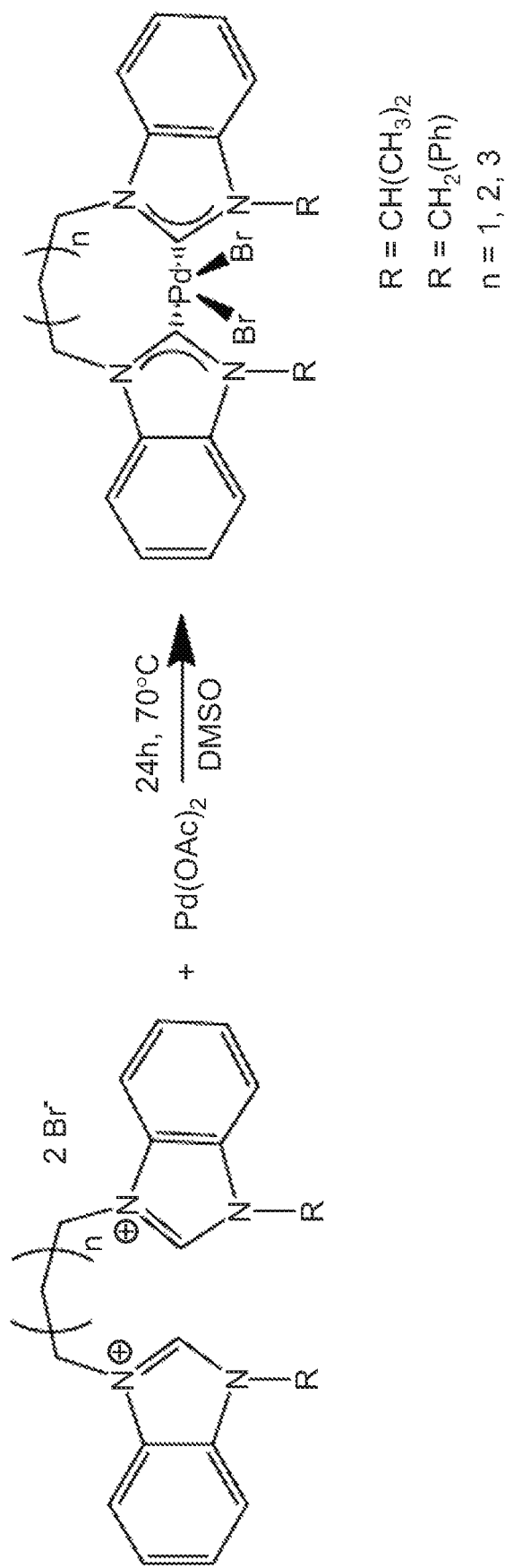
FIG. 12 shows an example reaction of a bridged NHC salt precursor with palladium acetate.

FIG. 12 shows an example reaction of an NHC salt precursor with palladium acetate to yield the bis-NHC—Pd (II) complexes C1, C2, and C3.

A round bottom flask (50 mL) was charged with 0.50 mmol of a bridged N-heterocyclic dicarbene ligand precursor (L1, L2 or L3), and 0.50 mmol of palladium(II) acetate. 15 mL of dimethyl sulfoxide was used as a solvent. The resulting orange solutions were heated to 70° C. for 24 h under stirring. The products were obtained as white precipitates. The precipitates were collected by filtration and washed twice with 15 mL of distilled water and then 15 mL of hexane. The residues were purified by extraction three times with dichloromethane/$H_2O$ (5 mL/5 mL). Finally, the dichloromethane extracts were evaporated under vacuum and the products were obtained as crystalline solids. Full characterization of the three complexes was accomplished by different physical and spectroscopic techniques such as $^1$H and $^{13}$C NMR, electrospray ionization—mass spectrometry, elemental analysis, and single crystal X-ray diffraction analysis.

Synthesis of Dibromido(1,1'-diisopropyl-3,3'-propylenedibenzimidazoline-2,2-diylidene)palladium(II) (complex C1) was performed as described above, with a 92% yield by mass of a white solid. Single crystals for complex C1 were obtained by slow crystallization procedure using a saturated solution of dichloromethane/acetonitrile (10:1 v/v). $^1$H NMR analysis (500 MHz, DMF-d7) yielded the following spectra in δ (ppm): 8.08 (2H, d, $^3$J=8.24 Hz, Ar—H, (the signals of aromatic protons overlap with solvent signal), 7.97 (2H, d, $^3$J=8.24 Hz, Ar—H), 7.45-7.37 (4H, m, Ar—H), 5.99 (2H, m, NCH), 5.43 (2H, m, $CH_2$), 5.11 (2H, m, $CH_2$), 2.19 (2H, m, $CH_2CH_2CH_2$), 1.94 [6H, d, $^3$J=6.71 Hz, $NC(CH_3)_2$], 1.78 [6H, d, $^3$J=5.80 Hz, $NC(CH_3)_2$]. $^{13}C\{^1H\}$ NMR analysis (125 MHz, $CD_2Cl_2$) yielded the following spectra in δ (ppm): 181 (Pd—C)[carbene signal ($NC_{binim}$N)], 135.2, 133.3, 132.3, 123.8, 123.7, 123.4, 123.1, 122.9, 113.2. 113, 110.7, 110.5 (Ar—H), 55.4 (NCH), 53.4 (NCH), 49.5 ($NCH_2$), 47.8 ($NCH_2$), 30.0 ($CH_2$), 28.5 ($CH_2$), 22.1, 21.7, 21.3 [$NC(CH_3)_2$].

The theoretical composition for complex C1 ($C_{23}H_{28}N_4Br_2Pd$, molecular weight 626.74) is 44.08% carbon; 4.50% hydrogen; and 8.94% nitrogen. Elemental analysis found 43.86% carbon, 4.25% hydrogen, and 8.63% nitrogen. Electrospray ionization yielded an m/z ratio of 547 with positive ionization.

Dibromido(1,1'-diisopropyl-3,3'-butylenedibenzimidazoline-2,2-diylidene)palladium(II) (complex C2) was synthesized as above, with a 68% yield by mass of an orange solid. $^1$H NMR analysis (400 MHz, $CDCl_3$) yielded the following spectra in δ (ppm): 8.49 (2H, d, $^3$J=7.28 Hz, Ar—H), 7.30 (2H, d, $^3$J=7.44 Hz Ar—H), 7.17-7.14 (4H, m, Ar—H), (the signals of aromatic protons overlap with solvent signal), 6.00-5.96 (2H, m, NCH), 5.75-5.71 (2H, m, $NCH_2$), 4.45-4.41 (2H, m, $NCH_2$), 1.80-1.45 (4H, m, $NCH_2CH_2$) (the signals of methylene protons were not assigned due to overlap with the isopropyl methyl signals), 1.74 [6H, d, $^3$J=6.56 Hz $(CH_3)_2$], 1.69 [6H, d, $^3$J=7.16 Hz $(CH_3)_2$]. $^{13}C\{^1H\}$ NMR analysis (125 MHz, $CD_2Cl_2$) yielded the following spectra in δ (ppm): 181.1 (Pd—C)[Carbene signal (NC$_{binim}$N)], 135.9, 132.9, 122.9, 122.8, 112.9, 111.0, (Ar—H), 48.2 (NCH), 30.1 (NCH$_2$), 27.7 (CH$_2$), 21.2 [NC(CH$_3$)$_2$].

The theoretical composition for this compound (C$_{24}$H$_{30}$N$_4$Br$_2$Pd, molecular weight 640.7) is 44.99% carbon, 4.72% hydrogen, and 8.74% nitrogen. Elemental analysis found 44.78% carbon, 4.89% hydrogen, and 8.53% nitrogen. Electrospray ionization yielded an m/z ratio of 561.00 with positive ionization.

Dibromido(1,1'-dibenzyl-3,3'-propylenedibenzimidazoline-2,2-diylidene)palladium(II) (complex C3) was synthesized as above, with a 73% yield by mass of white crystals. $^1$H analysis (400 MHz, CDCl$_3$) yielded the following spectra in δ (ppm): 7.10-7.69 (m, 2H, C—H-pyr), 7.48 (m, 4H, C—H— arom), 7.45-7.41 (m, 6H, C—H arom), 7.35-7.29 [m, 6H, C—H-(phenyl)], 5.87 (s, 4H, CH$_2$-Ph), 5.25 (m, 4H, NCH$_2$), 1.67 (m, 2H, NC(CH$_2$). $^{13}$C NMR analysis (125 MHz, CD$_2$Cl$_2$) yielded the following spectra in δ (ppm): 176.39 (Pd—C), 135.14, 134.96, 133.86, 129.08.

Example 4: X-Ray Crystallography of Complexes C1 and C3

Figure 13:
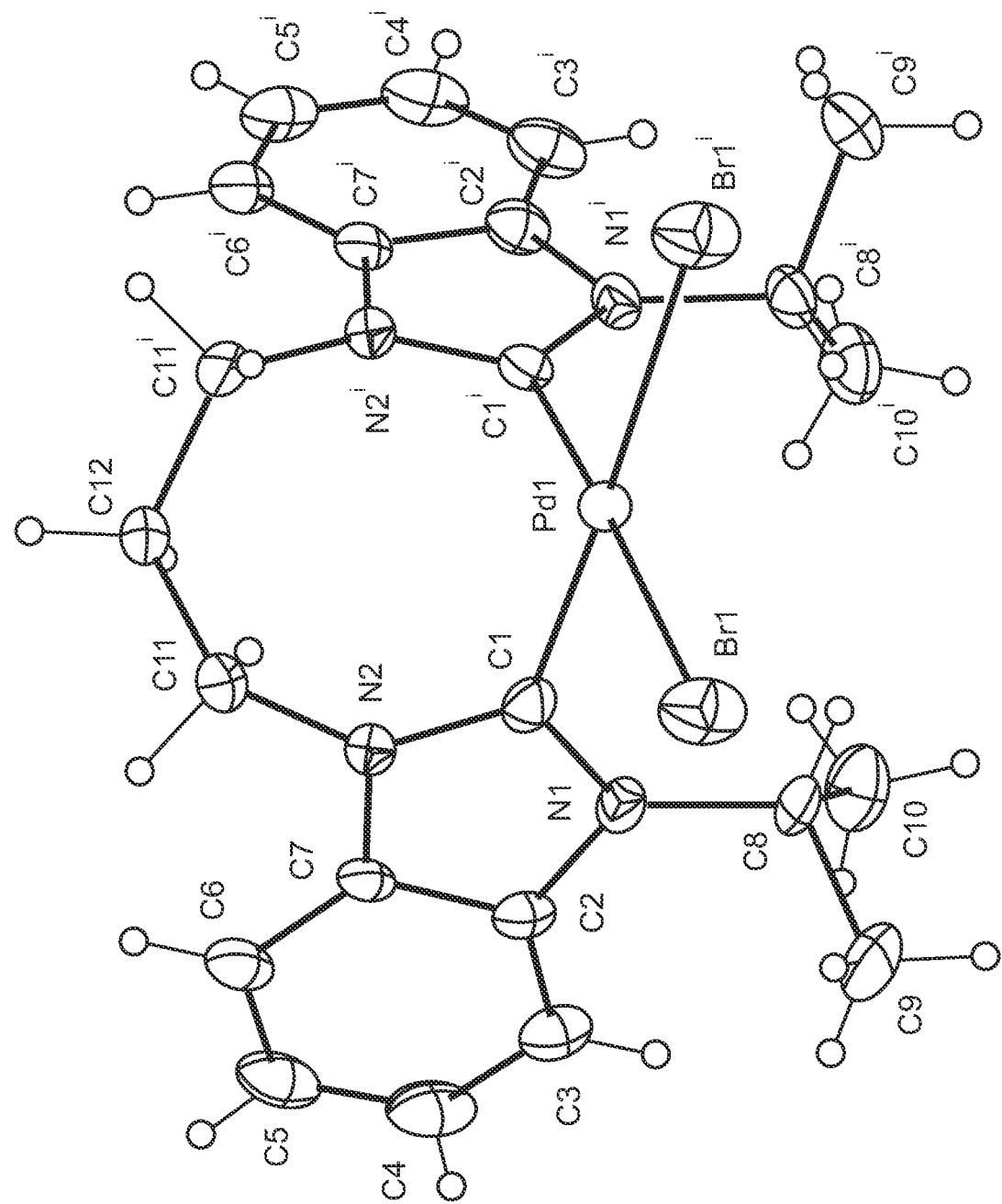
FIG. 13 shows an example ORTEP diagram of the molecular structure of complex C1.
Figure 14:
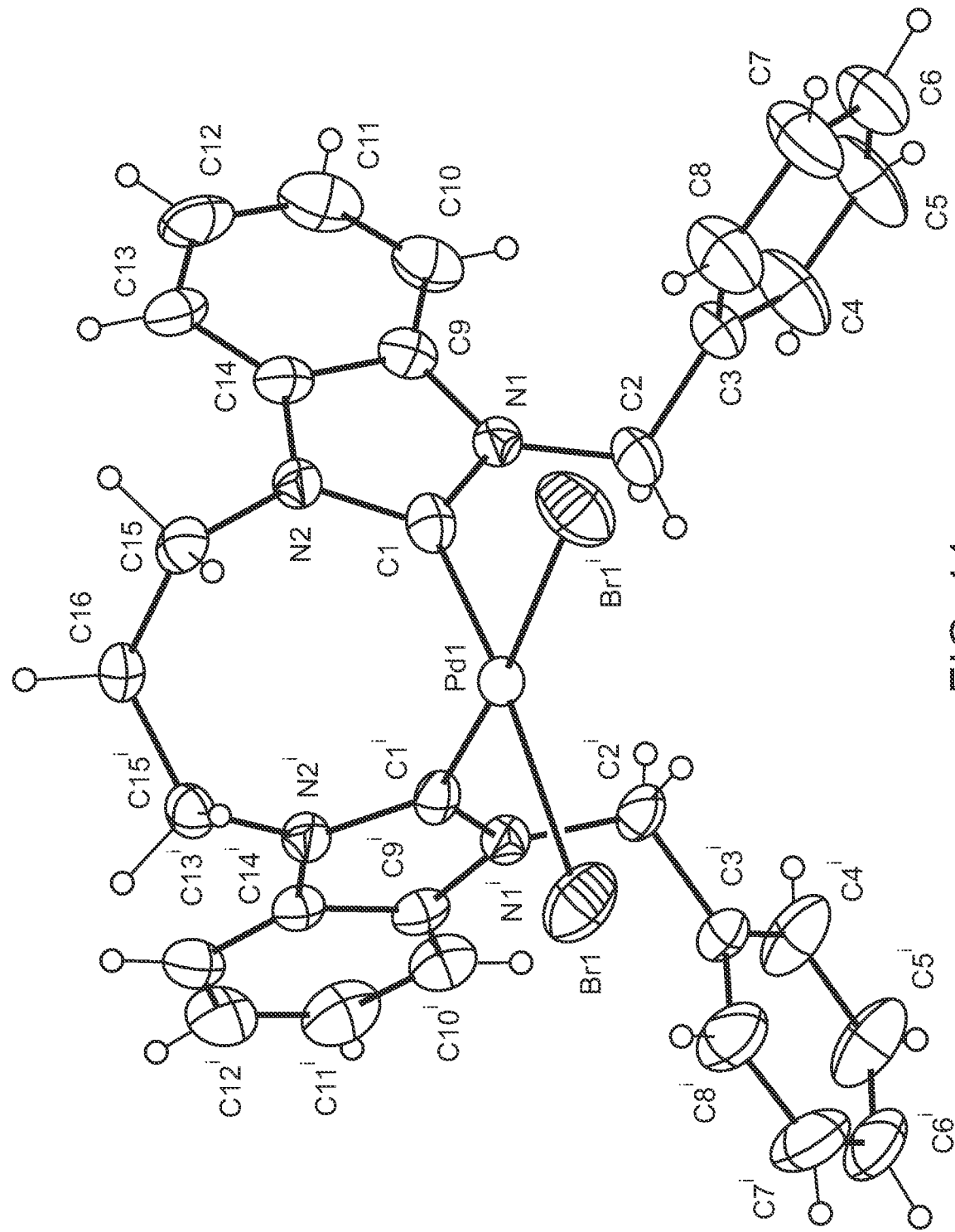
FIG. 14 shows an example ORTEP diagram of the molecular structure of complex C3.

Single crystal X-ray data collection for complexes C1 and C3 were performed at 298 K on a Bruker D8 Quest diffractometer (MoKα radiation λ=0.71073 Angstroms (Å)). Data were collected and integrated using Bruker APEX3 software package. Multi-scan absorption correction was performed using SADABS. The structures were solved by direct methods with SHELXS using SHELXTL package and refined using full-matrix least squares procedures on F2 via the program SHELXL-2014. ORTEP3 software was used for molecular graphics. The molecular structures of complexes C1 and C3 are depicted in example ORTEP diagrams in FIG. 13 and FIG. 14, respectively. All hydrogen atoms were included at calculated positions using a riding model. The thermal ellipsoids in FIGS. 13 and 14 are drawn at 30% probability level, with a symmetry code where i=x, −y+1/2, z. The crystal data and refinement details for C1 and C3 are given in Table 1. Selected bond lengths and bond angles are given in Table 2.

Complex C1 crystallized with one molecule, located on a mirror plane, in the asymmetric unit, as a dimethylformamide solvate while complex C3 crystallized with one molecule in the asymmetric unit as mixed hydrate/dichloromethane solvate. In both complexes the Pd(II) ion is coordinated by the chelating bridged bis-carbene ligand and two bromide ions at cis positions, in a distorted square planar geometry. The cis bond angles are in the ranges of 88.66 (17) −92.97 (2°) and 87.4 (3)° −97.01 (4°) in C1 and C3 respectively. The former is 1.997 (3) Å in C1 and in the range of (1.964 (8) Å-1.985 (8) Å) in C3 while the latter is 2.4906 (4) Å in C1 and in the range of (2.4659 (11) Å-2.4704 (11) Å) in C3. The chelate C—Pd—C bite angle values are 88.66 (17°) and (87.4 (3)°, 87.7 (3°) in C1 and C3, respectively. The larger bond distances in C1 are consistent with the larger steric hindrance of the isopropyl group opposing the formation of the chelate complex.

TABLE 1

Crystal and structure refinement data of complexes C1 and C3

| | C1 | C3 |
|---|---|---|
| CCDC Deposition # | 1961539 | 1950067 |
| Empirical formula | C$_{26}$H$_{35}$Br$_2$N$_5$OPd | C$_{32}$H$_{32}$Br$_2$Cl$_2$N$_4$OPd |
| Formula weight | 699.81 | 825.73 |
| Temperature (K) | 298(2) | 298(2) |
| Wavelength(Å) | 0.71073 | 0.71073 |
| Crystal system | Orthorhombic | Monoclinic |
| Space group | P nma | P 2$_1$/m |
| Unit cell dimensions | | |
| a (Å) | 16.2158(6) | 10.5561(8) |
| b (Å) | 18.1879(7) | 23.972(2) |
| c (Å) | 9.2992(4) | 13.3418(11) |
| α(°) | 90 | 90 |
| β(°) | 90 | 92.033(2) |
| γ(°) | 90 | 90 |
| Volume(Å$^3$) | 2742.63(19) | 3374.0(5) |
| Z | 4 | 4 |
| Density (calculated, g/cm$^3$) | 1.695 | 1.626 |
| Absorption coefficient (mm$^{-1}$) | 3.619 | 3.108 |
| F(000) | 1400 | 1640 |
| Theta range data collect. (°) | 2.512 to 28.371 | 2.564 to 28.367 |
| Index ranges | −21 ≤ h ≤ 21, −24 ≤ k ≤ 24, 12 ≤ l ≤ 12 | −14 ≤ h ≤ 14, −31 ≤ k ≤ 32, −17 ≤ l ≤ 17 |
| Reflection collected | 76298 | 123299 |
| Independent reflections | 3528 [R(int) = 0.0387] | 8604 [R(int) = 0.1448] |
| Absorption correction | Semi-empirical from equivalents | Semi-empirical from equivalents |
| Refinement method | Full-matrix least-sqaures on F$^2$ | Full-matrix least-squares on F$^2$ |
| Data/restraints/parameters | 3528/18/173 | 8604/6/399 |
| Goodness-of-fit on F$^2$ | 0.989 | 1.112 |
| Final R indices [I > 2sigma(I)] | R1 = 0.0342, wR2 = 0.1080 | R1 = 0.0716, wR2 = 0.1905 |
| R indices (all data) | R1 = 0.0473, wR2 = 0.1299 | R1 = 0.1308, wR2 = 0.2298 |
| Largest diff. peak and hole (c.Å$^3$) | 1.039 and −0.978 | 1.673 and −1.585 |

TABLE 2

Selected Bond lengths [Å] and bond angles [°] for complexes C1 and C3

| C1 | | C3 | |
|---|---|---|---|
| Pd(1)—C(1)#2 | 1.997(3) | Pd(1)—C(1) | 1.964(8) |
| Pd(1)—C(1) | 1.997(3) | Pd(1)—Br(1) | 2.4659(11) |
| Pd(1)—Br(1) | 2.4906(4) | Pd(2)—C(17) | 1.985(8) |
| Pd(1)—Br(1)#2 | 2.4906(4) | Pd(2)—Br(2) | 2.4704(11) |
| C(1)—N(2) | 1.344(4) | N(1)—C(1) | 1.352(10) |
| C(1)—N(1) | 1.350(4) | N(1)—C(9) | 1.395(10) |
| C(2)—N(1) | 1.397(4) | N(2)—C(1) | 1.355(9) |
| C(7)—N(2) | 1.388(4) | N(2)—C(14) | 1.372(9) |
| C(8)—N(1) | 1.475(4) | N(2)—C(15) | 1.458(9) |
| C(11)—N(2) | 1.469(4) | N(3)—C(17) | 1.339(10) |
| | | N(3)—C(25) | 1.373(9) |
| | | N(3)—C(18) | 1.463(9) |
| | | N(4)—C(17) | 1.339(8) |
| | | N(4)—C(30) | 1.401(9) |
| | | N(4)—C(31) | 1.452(9) |
| C(1)#2—Pd(1)—C(1) | 88.66(17) | C(1)—Pd1—C(1)#1 | 87.4(3) |
| C(1)#2—Pd(1)—Br(1) | 177.48(8) | C(1)—Pd(1)—Br(1) | 175.0(2) |
| C(1)—Pd(1)—Br(1) | 89.17(8) | C(1)#1—Pd(1)—Br(1) | 88.5(2) |
| C(1)#2—Pd(1)—Br(1)#2 | 89.17(8) | Br1—Pd1—Br1#1 | 95.49(4) |
| C(1)—Pd(1)—Br(1)#2 | 177.48(8) | C(17)#2—Pd(2)—C(17) | 87.7(3) |
| Br(1)—Pd(1)—Br(1)#2 | 92.97(2) | Br2#2—Pd(2)—Br(2) | 97.01(4) |
| | | C(17)—Pd(2)—Br(2) | 175.2(2) |
| | | C(17)#2—Pd(2)—Br(2) | 87.6(2) |

Symmetry codes: #1 = x,−y + 3/2,z  #2 = x,−y + 1/2,z

Example 5: Cyclocarbonylative Sonogashira Cross-Coupling Reaction with bis(NHC)Pd(II)Br$_2$ Complexes C1, C2, or C3

Figure 15:
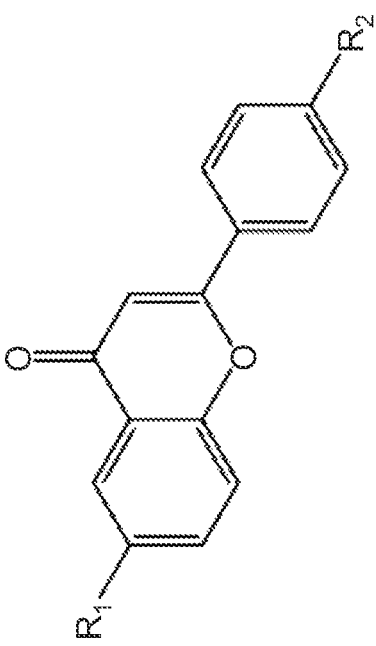
FIG. 15 shows an example reaction between a substituted 2-iodophenol and an aryl alkyne.
Figure 15:
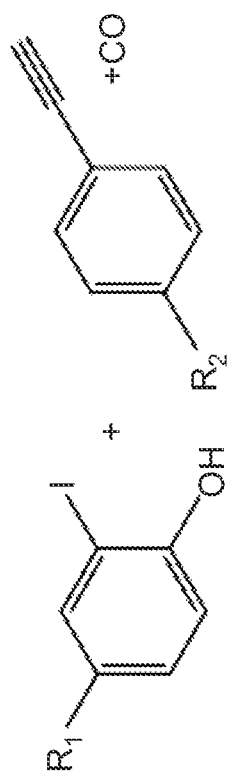

The bis(NHC)Pd(II)Br$_2$ complexes C1, C2, and C3 can catalyze a reaction between 2-iodophenols and aryl alkynes. For example, FIG. 15 shows an example reaction between a functionalized 2-iodophenol, for example functionalized 4'-hydroxy-3'-iodoaryl, and an aryl alkyne. The functional groups R$_1$ and R$_2$ can be electron withdrawing or electron donating functional groups, for example methoxy, hydrogen, nitro, methyl, tertiary butyl, phenyl or acetyl functional groups. Advantageously, the catalysts C1, C2, and C3 can be used with as little as 0.5 mol % in the reaction. The catalyzed reactions between a functionalized 2-iodophenol and an aryl alkyne were conducted with 0.50 mmol of functionalized 2-iodophenol, 0.55 mmol of an aryl alkyne, 1.00 mmol of diethylamine (Et$_2$NH), 3 mL of dimethylformamide (DMF), and 0.50 mol % of complex C1, C2, or C3. The reactants were added to a 45 mL stainless steel autoclave equipped with a glass liner, gas inlet valve and pressure gauge. The reaction was run for 16 hours at 100° C. under 100 psi of carbon monoxide gas. After the reaction, the autoclave was cooled to room temperature and excess carbon monoxide gas was discharged. The reaction products were extracted three times with 5 mL of distilled water and 10 mL of ethyl acetate. The ethyl acetate extracts were combined and concentrated in a rotary evaporator under reduced pressure. Flash chromatography was used to purify the reaction mixture using silica gel and an eluent (pentane-ethyl acetate in a 7:1 v/v ratio). Chromones and flavones (a type of aurone) were produced at high yields, between 86-91% isolated yield by mass percent. Table 3 shows example reactants and products for cyclocarbonylative Sonogashira coupling reactions catalyzed by complex C1, and the percent yield for these reactions. $^1$H NMR spectra were taken at 300 MHz in CDCl$_3$ at 24° C. $^{13}$C{$^1$H} spectra were taken at 75 MHz in CDCl$_3$ at 24° C.

TABLE 3

Cyclocarbonylative Sonogashira coupling reactions of 4'-hydroxy-3'-iodoaryls with aryl alkynes catalyzed by complex C1

| Example Reaction No. | 4'-hydroxy-3'-iodaryl | Aryl Alkyne | Product | Yield (% by mass) |
|---|---|---|---|---|
| 1 | [2-iodophenol structure with I and OH] | [4-ethynylanisole structure with OCH$_3$] | [flavone structure with OCH$_3$] | 91 |

TABLE 3-continued

Cyclocarbonylative Sonogashira coupling reactions of 4'-hydroxy-3'-iodoaryls with aryl alkynes catalyzed by complex C1

| Example Reaction No. | 4'-hydroxy-3'-iodaryl | Aryl Alkyne | Product | Yield (% by mass) |
|---|---|---|---|---|
| 2 | | | | 86 |
| 3 | | | | 88 |
| 4 | | | | 93 |
| 5 | | | | 98 |
| 6 | | | | 95 |
| 7 | | | | 91 |

TABLE 3-continued

Cyclocarbonylative Sonogashira coupling reactions of 4'-hydroxy-3'-iodoaryls with aryl alkynes catalyzed by complex C1

| Example Reaction No. | 4'-hydroxy-3'-iodaryl | Aryl Alkyne | Product | Yield (% by mass) |
|---|---|---|---|---|
| 8 | (structure) | (structure) | (structure) | 93 |

Example 6: Cyclocarbonylative Sonogashira Cross-Coupling Reaction with Pd-bis(NHC)Br$_2$ Complexes C1, C2, or C3

Figure 16:
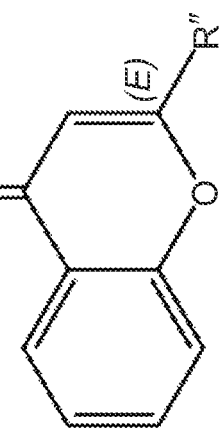
FIG. 16 shows an example reaction between a substituted 2-iodophenol and an alkyl alkyne.
Figure 16:
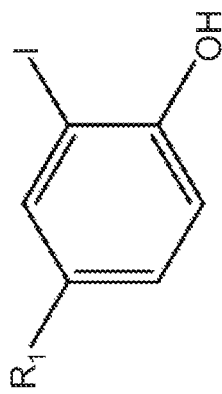

The bis(NHC)Pd(II)Br$_2$ complexes C1, C2, and C3 can each catalyze the reaction between 2-iodophenols and an alkyl alkyne. For example, FIG. 16 shows an example reaction between a functionalized 2-iodophenol and an alkyl alkyne. The functional groups R$_1$ and R" can be electron withdrawing or electron donating functional groups, for example methoxy, hydrogen, nitro, methyl, tertiary butyl, phenyl or acetyl functional groups. Advantageously, the catalysts C1, C2, and C3 can be used with as little as 0.5 mol % in the reaction. The catalyzed reactions between a functionalized 2-iodophenol and an alkyl alkyne were conducted with 0.50 mmol of functionalized 2-iodophenol, 0.60 mmol of an alkyl alkyne, 1.00 mmol of Et$_2$NH, 2.5 mL of DMF, and 0.50 mol % of complex C1. The reactants were added to a 45 mL stainless steel autoclave equipped with a glass liner, gas inlet valve and pressure gauge. The reaction was run for 24 hours at 110° C. under 100 psi of carbon monoxide. After the reaction, the autoclave was cooled to room temperature and excess carbon monoxide gas was discharged. The reaction products were extracted three times with 5 mL of distilled water and 10 mL of ethyl acetate. The ethyl acetate extracts were combined and concentrated in a rotary evaporator under reduced pressure. Flash chromatography was used to purify the reaction mixture using silica gel and an eluent (pentane-ethyl acetate in a 7:1 v/v ratio). Chromones and flavones were produced at high yields, between 53-90% by mass. Table 4 shows example reactants and products for cyclocarbonylative Sonogashira coupling reactions catalyzed by complex C1, and the percent yield for these reactions.

TABLE 4

Cyclocarbonylative Sonogashira coupling reactions of 4'-hydroxy-3'-iodoaryls with alkyl alkynes catalyzed by complex C1.

| Example Reaction No. | 4'-hydroxy-3'-iodoaryls | Alkyl Alkyne | Product | Yield (% by mass) |
|---|---|---|---|---|
| 9 | (structure) | (structure) | (structure) | 81 |
| 10 | (structure) | (structure) | (structure) | 68 |
| 11 | (structure) | (structure) | (structure) | 53 |

TABLE 4-continued

Cyclocarbonylative Sonogashira coupling reactions of 4'-hydroxy-3'-iodoaryls with alkyl alkynes catalyzed by complex C1.

| Example Reaction No. | 4'-hydroxy-3'-iodoaryls | Alkyl Alkyne | Product | Yield (% by mass) |
|---|---|---|---|---|
| 12 | | | | 71 |
| 13 | | | | 77 |
| 14 | | | | 90 |

Example 6: Regioselectivity of Complexes C1, C2, and C3

Cyclocarbonylative Sonogashira coupling reactions of a 2-iodophenol with phenylacetylene can illustrate the selectivity of the complexes C1, C2, and C3. An example reaction of 2-iodophenol (compound 1a) and phenylacetylene (compound 2a) under carbon monoxide in the presence of a catalytic amount of C1 was analyzed (Eq. 1). Table 5 shows the selectivity of the complexes under these conditions.

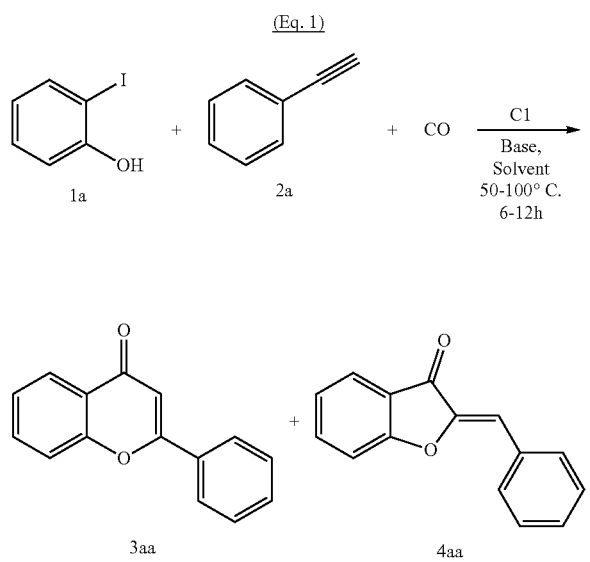

(Eq. 1)

TABLE 5

Cyclocarbonylative Sonogashira coupling reactions of 2-iodophenol (1a) with phenylacetylene (2a).

| | | Selectivity %[b] | |
|---|---|---|---|
| Catalyst (mol%) | Conversion (%)[b] | 3aa (%)[c] | 4aa (%)[c] |
| C1 (0.5%) | 98 | 96 (92) | 4 |
| C2 (0.5%) | 88 | 96 (85) | 4 |
| C3 (0.5%) | 84 | 95 (79) | 5 |

[a]Reaction conditions: [Pd] (mol %), 2-iodophenol (0.5 mmol), phenylacetylene (0.6 mmol), Et$_2$NH (1.0 mmol), DMF (2.5 mL), CO (100 psi), 100° C., 16 h.
[b]Determined by gas chromatography (GC) and gas chromatography - mass spectrometry (GC-MS).
[c]Isolated yield.
[d]THF was used as a solvent.

The selectivity of the complexes is dependent on the reaction conditions. Table 6 shows varied conditions for the reaction in Equation 1, catalyzed by complex C1. For example, the reactions were conducted at room temperature, 80° C., or 100° C., and the base and solvent were varied. The results of these reactions are summarized in Table 6. Only traces of 2-phenyl-4H-chromen-4-one (compound 3aa) were obtained when a neat reaction was conducted using 1.0 mol of C1 as a catalyst and diethylamine (Et$_2$NH) as a base at room temperature for 16 hours (Table 6, Example Reaction 15). However, a conversion of 59.5% was obtained at 80° C. and a high conversion (85.5%) was achieved at 100° C. These reactions produced 2-phenyl-4H-chromen-4-one (compound 3aa) as a major compound. The isolated yield of compound 3aa gradually increased by increasing the temperature (Table 6, Example Reactions 16-17). When diethylamine (Et$_2$NH) in the neat reaction was replaced by trimethylamine (Et$_3$N) at 80° C. and 100° C. using C1, the cyclocarbonylative reaction of 2-iodophenols with phenylacetylene led to a six member ring product flavone (compound 3aa) and five membered ring product aurone (compound 4aa). Moreover, the increase of the temperature from 80° C. to 100° C. increased the conversion from 85% to 100% and favored the formation of the aurone product compound 4aa (57% and 66%) (Table 6, Example Reactions 18-19). However, when tetrahydrofuran (THF) was used as a solvent at 80° C. and 100° C., with triethylamine as a solvent, the conversions dropped to 69% and 93%, respectively, with only smalls changes in the regioselectivity (Table 6, Example Reactions 20 and 21). Nevertheless, the use of Et$_2$NH as a base with THF as solvent at 80° C. and 100° C. led to higher conversions (68% and 84.5%) (Table 6, Example Reactions 22 and 23). Accordingly, under the same experimental conditions, triethylamine oriented the cyclocarbonylative Sonogashira reactions towards the production of aurone compound 4aa as the major product. In addition, diethylamine in THF produced flavone compound 3aa in high isolated yields. When potassium carbonate was used as a base in THF at 100° C. (Table 6, Example Reaction 24), a full conversion was observed to produce flavone compound 3aa and aurone compound 4aa (38/62). In toluene as a solvent, the cyclocarbonylative Sonogashira reaction of 2-iodophenol with phenylacetylene under the conditions in Example Reaction 25 (Et$_2$NH/1.0% mol of C1/100° C./16 h) was converted (97%) and led to the two products flavone compound 3aa and aurone compound 4aa with a ratio of 93/7. In THF as a solvent and Et$_2$NH as a base, the catalyst's C1 loading can be decreased from 1.0 mol % to 0.5 mol % of C1 leading to high conversion (80%) to produce flavone compound 3aa as the only product of the reaction (Table 6, Example Reaction 26). An isolated yield of 2-phenyl-4H-chromen-4-one (compound 3aa, 96%) was achieved with 98% conversion of 2-iodophenol when the DMF was used as solvent under the conditions in Example Reaction 27 [Et$_2$NH/C1 (0.5 mol %)/100° C./16 h]. Small amounts of aurone compound 4aa were also obtained (compound 3aa/compound 4aa=96/4). A decrease in the temperature from 100° C. to 80° C. and 50° C. [DMF/Et$_2$NH/C1 (0.5 mol %)/16 h] demonstrated a gradual decline in the conversion of 2-iodophenol (83% at 80° C. and 38% at 50° C.) and the isolated yields of the flavone compound 3aa were 81% at 80° C. and 35% at 50° C. (Table 6, Example Reactions 28 and 29). Therefore, 100° C. can be considered as an optimized temperature for the subsequent catalytic reactions. The effect of the reaction time was also studied. After 16 h, 12 h and 6 h the isolated yields of the flavone compound 3aa decreased from 92% to 72% and 46%, respectively (Table 6, Example Reactions 27, 30, 31). When DMF was replaced by other solvents such as THF, toluene and in the neat Et$_2$NH [Et$_2$NH/C1 (0.5 mol %)/100° C./16 h], a significant decrease in the conversions and isolated yields in flavone were observed (Table 6, Example Reactions 32-34).

Additionally, the study of the role of the base on the regioselectivity was also conducted using Et$_3$N and K$_2$CO$_3$ as bases with DMF as solvent [C1 (0.5 mol %)/100° C./16 h]. For example, the use of K$_2$CO$_3$ as a base produced a mixture of flavone compound 3aa and aurone compound 4aa (70/30) (Table 6, Example Reaction 35). Similarly, the use of trimethylamine gave lower regioselectivity, producing a mixture of flavone compound 3aa and aurone compound 4aa (60/40) (Table 6, Example Reaction 36). When Et$_3$N was used with THF as a solvent, the isolated yield in flavone compound 3aa dropped to 30% (Table 6, Example Reaction 21) and increased with DMF to 54% (Table 6, Example Reaction 37). These results showed the importance of Et$_2$NH and DMF as regioselective factors in the production of flavones.

TABLE 6

Cyclocarbonylative Sonogashira coupling reactions of 2-iodophenol (compound 1a) with phenylacetylene (compound 2a) by complex C1.

| Example Reaction No. | C1 mol % | Base | Solvent | T (° C.) | Time (h) | Conv. (%)$^b$ | Selectivity (%)$^b$ 3aa (%)$^c$ | 4aa (%)$^c$ |
|---|---|---|---|---|---|---|---|---|
| 15 | 1.0 | Et$_2$NH | Et$_2$NH | RT | 16 | traces | traces | traces |
| 16 | 1.0 | Et$_2$NH | Et$_2$NH | 80 | 16 | 59.5 | 100 (55) | — |
| 17 | 1.0 | Et$_2$NH | Et$_2$NH | 100 | 16 | 85.5 | 100 (82) | — |
| 18 | 1.0 | Et$_3$N | Et$_3$N | 80 | 16 | 85 | 43 (34) | 57 (45) |
| 19 | 1.0 | Et$_3$N | Et$_3$N | 100 | 16 | 100 | 34 (30) | 66 (63) |
| 20 | 1.0 | Et$_3$N | THF | 80 | 16 | 69 | 40 (25) | 60 (38) |
| 21 | 1.0 | Et$_3$N | THF | 100 | 16 | 93 | 36 (30) | 64 (56) |
| 22 | 1.0 | Et$_2$NH | THF | 80 | 16 | 68 | 100 (64) | — |
| 23 | 1.0 | Et$_2$NH | THF | 100 | 16 | 84.5 | 100 (81) | — |
| 24 | 1.0 | K$_2$CO$_3$ | THF | 100 | 16 | 96 | 38 (33) | 62 (57) |
| 25 | 1.0 | Et$_2$NH | Toluene | 100 | 16 | 97 | 93 (88) | 7 |
| 26 | 0.5 | Et$_2$NH | THF | 100 | 16 | 80 | 100 (77) | — |
| 27 | 0.5 | Et$_2$NH | DMF | 100 | 16 | 98 | 96 (92) | 4 |
| 28 | 0.5 | Et$_2$NH | DMF | 80 | 16 | 83 | 100 (81) | — |
| 29 | 0.5 | Et$_2$NH | DMF | 50 | 16 | 38 | 100 (35) | — |
| 30 | 0.5 | Et$_2$NH | DMF | 100 | 12 | 76 | 100 (72) | — |
| 31 | 0.5 | Et$_2$NH | DMF | 100 | 6 | 49 | 100 (46) | — |
| 32 | 0.5 | Et$_2$NH | THF | 100 | 16 | 72 | 100 (70) | — |
| 33 | 0.5 | Et$_2$NH | Toluene | 100 | 16 | 82 | 95 (76) | 5 |
| 34 | 0.5 | Et$_2$NH | Et$_2$NH | 100 | 16 | 79 | 100 (76) | — |
| 35 | 0.5 | K$_2$CO$_3$ | DMF | 100 | 16 | 97 | 70 (65) | 30 (27) |
| 36 | 0.5 | Et$_3$N | DMF | 100 | 16 | 95 | 60 (54) | 40 (35) |

$^a$Reaction conditions: complex C1 (mol %), 2-iodophenol (0.5 mmol), phenylacetylene (0.6 mmol), base (1.0 mmol), solvent (2.5 mL), CO (100 psi), 100° C.
$^b$Determined by GC and GC-MS.
$^c$Isolated yield.

The following units of measure have been mentioned in this disclosure:

| Unit of Measure | Full form |
|---|---|
| hr | hour |
| cv | degree Celsius |
| mol | mole |
| mol % | catalytic loading, (mol catalyst/mol reactant) × 100 |
| mmol | milimole |
| psi | pounds per square inch |
| Å | Angstrom |
| g | gram |

| Unit of Measure | Full form |
|---|---|
| Unit of Measure | Full form |
| cm³ | cubic centimeter |
| mm | milimeter |

In some implementations, a compound of Formula C3 has the following structure:

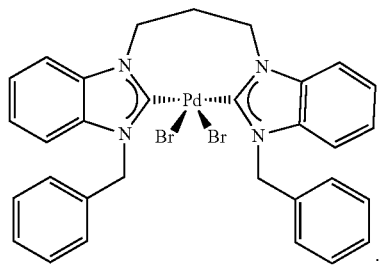

In some implementations, a method of synthesizing a palladium catalyst includes reacting a benzimidazole with a halogenated hydrocarbon in the presence of a base and acetonitrile to produce an alkyl-1H-benzo[d]imidazole, reacting the alkyl-1H-benzo[d]imidazole with a halogenated crosslinking chain to produce a bridged N-heterocyclic carbene salt precursor, and reacting the bridged N-heterocyclic carbene with palladium acetate.

This aspect, taken alone or combinable with any other aspect, can include the following features. Reacting a benzimidazole with a halogenated hydrocarbon includes reacting at 80° C. for 24 hours.

This aspect, taken alone or combinable with any other aspect, can include the following features. Reacting the alkyl-1H-benzo[d]imidazole with a halogenated crosslinking chain includes reacting at 103° C. for 24 hours in 1,4-dioxane.

This aspect, taken alone or combinable with any other aspect, can include the following features. Reacting the N-heterocyclic carbene with palladium acetate includes reacting at 70° C. for 24 hours in dimethyl sulfoxide.

This aspect, taken alone or combinable with any other aspect, can include the following features. The halogenated hydrocarbon is a branched halogenated alkyl group.

This aspect, taken alone or combinable with any other aspect, can include the following features. The branched halogenated alkyl group is isopropyl bromide.

This aspect, taken alone or combinable with any other aspect, can include the following features. The halogenated hydrocarbon is benzyl bromide.

This aspect, taken alone or combinable with any other aspect, can include the following features. The halogenated crosslinking chain is a di-halido unbranched alkyl chain.

This aspect, taken alone or combinable with any other aspect, can include the following features. The di-halido unbranched alkyl chain is 1,3-dibromopropane, 1,4-dibromobutane, or 1,5-dibromopentane.

In some implementations, a method of synthesizing chromones or aurones includes reacting a 2-iodophenol and an aryl alkyne in the presence of a palladium catalyst, wherein the palladium catalyst includes at least one of Formula C1, Formula C2, or Formula C3, where Formula C1 has the structure

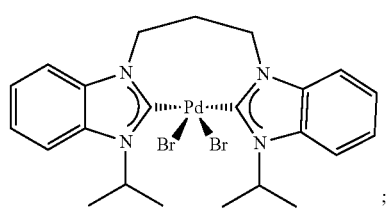

Formula C2 has the structure

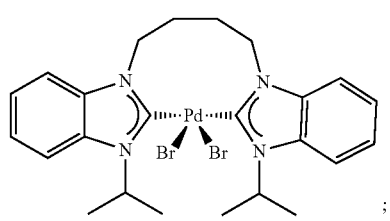

and
Formula C3 has the structure

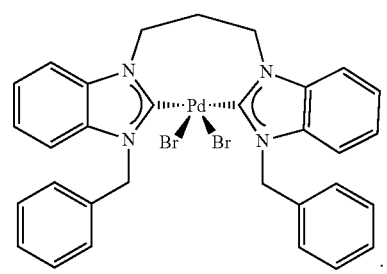

This aspect, taken alone or combinable with any other aspect, can include the following features. Reacting the 2-iodophenol and the aryl alkyne in the presence of a palladium catalyst includes reacting the 2-iodophenol and the aryl alkyne in the presence of 0.5 mol % of the palladium catalyst.

This aspect, taken alone or combinable with any other aspect, can include the following features. Reacting the 2-iodophenol and the aryl alkyne in the presence of a palladium catalyst includes reacting the 2-iodophenol and the aryl alkyne with 2 equivalents diethylamine in dimethylformamide, and the reaction takes place under carbon monoxide at 100 psi for 16 hours at 100° C.

This aspect, taken alone or combinable with any other aspect, can include the following features. The 2-iodophenol is functionalized with an electron withdrawing group.

This aspect, taken alone or combinable with any other aspect, can include the following features. The aryl alkyne is functionalized with an electron withdrawing group.

In some implementations, a method of synthesizing chromones or aurones includes reacting a 2-iodophenol and an alkyl alkyne in the presence of a palladium catalyst, wherein the palladium catalyst includes at least one of Formula C1, Formula C2, or Formula C3, where Formula C1 is Formula (C2) is

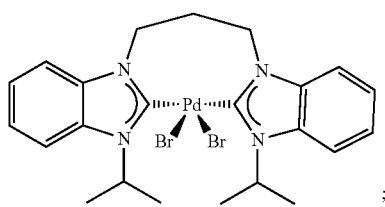

and
Formula (C3) is

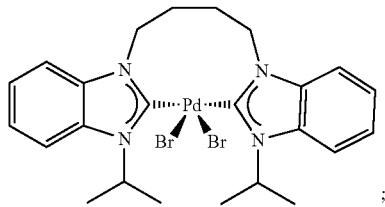

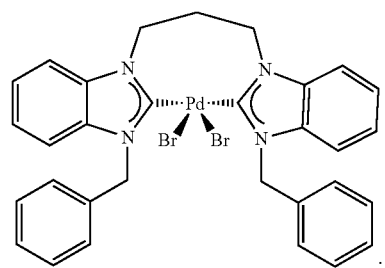

This aspect, taken alone or combinable with any other aspect, can include the following features. Reacting the 2-iodophenol and the alkyl alkyne in the presence of a palladium catalyst includes reacting the 2-iodophenol and the alkyl alkyne in the presence of 0.5 mol % of the palladium catalyst.

This aspect, taken alone or combinable with any other aspect, can include the following features. Reacting the 2-iodophenol and the alkyl alkyne in the presence of a palladium catalyst includes reacting the 2-iodophenol and the alkyl alkyne with 2 equivalents diethylamine in dimethylformamide, and wherein the reaction takes place under carbon monoxide at 100 psi for 24 hours at 110° C.

This aspect, taken alone or combinable with any other aspect, can include the following features. The 2-iodophenol is functionalized with an electron withdrawing group.

This aspect, taken alone or combinable with any other aspect, can include the following features. The alkyl alkyne is functionalized with an electron withdrawing group.

The term "about" as used in this disclosure can allow for a degree of variability in a value or range, for example, within 10%, within 5%, or within 1% of a stated value or of a stated limit of a range.

The term "solvent" as used in this disclosure refers to a liquid that can dissolve a solid, another liquid, or a gas to form a solution. Non-limiting examples of solvents are silicones, organic compounds, water, alcohols, ionic liquids, and supercritical fluids.

As used in this disclosure, "weight percent" (wt %) can be considered a mass fraction or a mass ratio of a substance to the total mixture or composition. Weight percent can be a weight-to-weight ratio or mass-to-mass ratio, unless indicated otherwise.

A number of implementations of the disclosure have been described. Nevertheless, it will be understood that various modifications may be made without departing from the spirit and scope of the disclosure.

What is claimed is:

1. A method of synthesizing chromones or aurones comprising reacting a 2-iodophenol and an aryl alkyne in the presence of a palladium catalyst under a carbon monoxide atmosphere, wherein the palladium catalyst comprises at least one of Formula (C1), Formula (C2), or Formula (C3), wherein Formula (C1) is

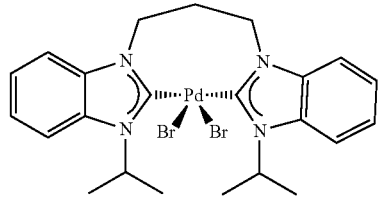

Formula (C2) is

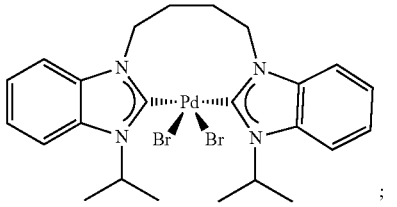

; and

Formula (C3) is

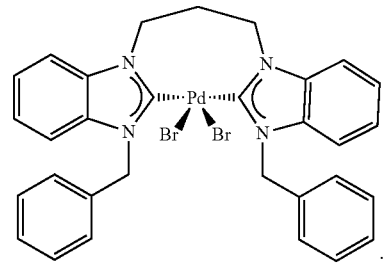

2. The method of claim 1, wherein reacting the 2-iodophenol and the aryl alkyne in the presence of a palladium catalyst comprises reacting the 2-iodophenol and the aryl alkyne in the presence of 0.5 mol % of the palladium catalyst.

3. The method of claim 1, wherein reacting the 2-iodophenol and the aryl alkyne in the presence of a palladium catalyst comprises reacting the 2-iodophenol and the aryl alkyne with 2 equivalents diethylamine in dimethylformamide, and wherein the reacting takes place under carbon monoxide at 100 psi for 16 hours at 100° C.

4. The method of claim 1, wherein the aryl alkyne is functionalized with an electron withdrawing group.

* * * * *